United States Patent
Gillies et al.

(10) Patent No.: US 6,272,370 B1
(45) Date of Patent: Aug. 7, 2001

(54) MR-VISIBLE MEDICAL DEVICE FOR NEUROLOGICAL INTERVENTIONS USING NONLINEAR MAGNETIC STEREOTAXIS AND A METHOD IMAGING

(75) Inventors: George T. Gillies, Earlysville, VA (US); John Kucharczyk, Minneapolis, MN (US); William C. Broaddus, Midlothian, VA (US); Richard Latchaw, Miami, FL (US)

(73) Assignees: The Regents of University of Minnesota, MN; Virginia Commonwealth University, Virginia ( * ) Notice: Subject to any disclaimer, the term of this patent is extended or adjusted under 35 U.S.C. 154(b) by 0 days.

(21) Appl. No.: 09/131,031

(22) Filed: Aug. 7, 1998

(51) Int. Cl.[7] ............................................. A61B 5/05
(52) U.S. Cl. ..................... 600/411; 600/417; 600/423; 600/424; 600/427; 600/429; 600/420; 606/130; 324/309; 324/318; 604/508; 604/510
(58) Field of Search ....................... 600/411, 409, 600/410, 417, 423, 424, 427, 429, 420; 324/318, 309; 604/508, 510; 606/130

(56) References Cited

U.S. PATENT DOCUMENTS

| | | | |
|---|---|---|---|
| D. 298,190 | 10/1988 | Komai et al. | D6/380 |
| D. 329,335 | 9/1992 | Komai et al. | D6/361 |
| D. 329,338 | 9/1992 | Komai et al. | D6/370 |
| D. 333,042 | 2/1993 | Komai et al. | D6/370 |
| 3,055,370 | 9/1962 | McKinney et al. | 128/303 |
| 3,554,186 | 1/1971 | Leksell et al. | 128/2 |
| 3,705,938 | 12/1972 | Hyman et al. | 424/19 |
| 3,857,934 | 12/1974 | Bernstein et al. | 424/30 |
| 3,868,956 | 3/1975 | Alfidi et al. | 128/345 |
| 3,986,703 | 10/1976 | Brett et al. | 254/173 R |

(List continued on next page.)

FOREIGN PATENT DOCUMENTS

| | | | |
|---|---|---|---|
| 0442329 | 8/1991 | (EP) | G01D/5/18 |
| 93/15784 | 8/1993 | (WO) | A61M/25/00 |
| 93/15785 | 8/1993 | (WO) | A61M/25/00 |

(List continued on next page.)

OTHER PUBLICATIONS

Cares, H.L., et al., "Laboratory experience with a magnetically guided intravascular catheter system", *Journal of Neurosurgery*, 38, (2), 145–154, (Feb. 1973).

Chandler, W.F., et al., "Use of Implantable Pump System for Intraarterial, Intraventricular and Intratumoral Treatment of Malignant Brain Tumors", *Annals of the New York Acadamy of Sciences*, 531, Neurological Applications of Implanted Drug Pumps, 206–212, (1988).

Driller, J., et al., "A review of medical applications of magnet attraction and detection", *Journal of Medical Engineering & Technology*, 11 (6), 271–277, (Nov./Dec. 1987).

(List continued on next page.)

*Primary Examiner*—Marvin M. Lateef
*Assistant Examiner*—Jeoyuh Lin
(74) *Attorney, Agent, or Firm*—Mark A. Litman & Assoc.

(57) ABSTRACT

The present invention comprises a device and method for targeted drug delivery, and especially intracranial inflsion or retroperfusion drug delivery using nonlinear magnetic stereotaxis in combination with magnetic resonance (MR) imaging and/or X-ray visualization. An MR-visible and/or X-ray visible drug delivery device is positioned by non-linear magnetic stereotaxis at a site such as an intracranial target site, its location is verified via MR imaging, and it is then used to deliver a biologically active material such as a diagnostic or therapeutic drug solution into that site (such as the brain) at constant or variable rates. The spatial distribution kinetics of the injected or infsed drug agent may be monitored quantitatively and non-invasively using real-time MR-imaging such as water proton directional diffusion MR imaging, to establish the efficacy of targeted drug delivery.

21 Claims, 3 Drawing Sheets

U.S. PATENT DOCUMENTS

| | | | |
|---|---|---|---|
| 4,023,175 | 5/1977 | Brown et al. | 343/17 |
| 4,147,161 | 4/1979 | Ikebe et al. | 128/2 R |
| 4,259,703 | 3/1981 | Young et al. | 360/113 |
| 4,284,948 | 8/1981 | Young | 324/309 |
| 4,284,950 | 8/1981 | Burl et al. | 324/320 |
| 4,300,096 | 11/1981 | Harrison et al. | 324/309 |
| 4,316,106 | 2/1982 | Young et al. | 307/481 |
| 4,338,571 | 7/1982 | Young | 330/84 |
| 4,338,945 | 7/1982 | Kosugi et al. | 128/421 |
| 4,339,716 | 7/1982 | Young et al. | 324/309 |
| 4,355,282 | 10/1982 | Young et al. | 324/309 |
| 4,361,807 | 11/1982 | Burl et al. | 324/309 |
| 4,362,993 | 12/1982 | Young et al. | 324/309 |
| 4,379,262 | 4/1983 | Young | 324/309 |
| 4,384,255 | 5/1983 | Young et al. | 324/309 |
| 4,418,316 | 11/1983 | Young et al. | 324/309 |
| 4,448,195 | 5/1984 | LeVeen et al. | 128/344 |
| 4,449,097 | 5/1984 | Young et al. | 324/309 |
| 4,454,474 | 6/1984 | Young | 324/309 |
| 4,458,203 | 7/1984 | Young | 324/309 |
| 4,503,569 | 3/1985 | Dotter | 3/1.4 |
| 4,520,828 | 6/1985 | Burl et al. | 128/653 |
| 4,534,358 | 8/1985 | Young | 128/653 |
| 4,553,122 | 11/1985 | Young | 335/296 |
| 4,554,925 | 11/1985 | Young | 128/653 |
| 4,558,278 | 12/1985 | Young | 324/309 |
| 4,563,647 | 1/1986 | Young et al. | 324/309 |
| 4,564,813 | 1/1986 | Young | 324/311 |
| 4,572,198 | 2/1986 | Codrington | 128/653 |
| 4,587,488 | 5/1986 | Young | 324/306 |
| 4,604,578 | 8/1986 | Young | 324/307 |
| 4,607,221 | 8/1986 | Young | 324/306 |
| 4,608,977 | 9/1986 | Brown | 128/303 B |
| 4,631,480 | 12/1986 | Young | 324/309 |
| 4,631,481 | 12/1986 | Young | 324/320 |
| 4,642,568 | 2/1987 | Young | 324/309 |
| 4,644,275 | 2/1987 | Young | 324/307 |
| 4,646,023 | 2/1987 | Young | 324/309 |
| 4,683,432 | 7/1987 | Young | 324/309 |
| 4,703,269 | 10/1987 | Young | 324/309 |
| 4,710,403 | 12/1987 | Krause et al. | 427/304 |
| 4,727,873 | 3/1988 | Mobin-Uddin | 128/303 R |
| 4,733,183 | 3/1988 | Young | 324/309 |
| 4,760,337 | 7/1988 | Young | 324/309 |
| 4,767,973 | 8/1988 | Jacobsen et al. | 318/652 |
| 4,775,556 | 10/1988 | Krause et al. | 427/272 |
| 4,805,615 | 2/1989 | Carol | 128/303 B |
| 4,807,620 | 2/1989 | Strul et al. | 128/303.1 |
| 4,824,436 | 4/1989 | Wolinsky | 604/53 |
| 4,827,931 * | 5/1989 | Longmore | 606/148 |
| 4,864,240 | 9/1989 | Young | 324/318 |
| 4,869,247 | 9/1989 | Howard, III et al. | 128/303.1 |
| 4,882,560 | 11/1989 | Young et al. | 335/299 |
| 4,885,448 | 12/1989 | Kasner et al. | 219/121.69 |
| 4,892,538 | 1/1990 | Aebischer et al. | 604/891.1 |
| 4,914,608 | 4/1990 | LeBihan et al. | 364/557 |
| 4,922,924 | 5/1990 | Gambale et al. | 128/772 |
| 4,941,874 | 7/1990 | Sandow et al. | 604/60 |
| 4,951,064 | 8/1990 | Kun et al. | 346/107 R |
| 4,955,891 | 9/1990 | Carol | 606/130 |
| 4,973,304 | 11/1990 | Graham et al. | 604/48 |
| 4,989,608 | 2/1991 | Ratner | 128/653 A |
| 4,994,069 | 2/1991 | Ritchart et al. | 606/191 |
| 4,994,071 | 2/1991 | MacGregor | 606/194 |
| 4,998,539 | 3/1991 | Delsanti | 128/898 |
| 4,998,938 | 3/1991 | Ghajar et al. | 606/130 |
| 5,015,955 | 5/1991 | Young | 324/309 |
| 5,017,566 | 5/1991 | Bodor | 514/58 |
| 5,017,824 | 5/1991 | Phillips et al. | 313/13 |
| 5,018,173 | 5/1991 | Komai et al. | 378/4 |
| 5,033,998 * | 7/1991 | Corday et al. | 600/18 |
| 5,034,691 | 7/1991 | Young | 324/309 |
| 5,035,231 | 7/1991 | Kubokawa et al. | 128/6 |
| 5,035,706 | 7/1991 | Giantureo et al. | 606/198 |
| 5,036,282 | 7/1991 | Morich et al. | 324/318 |
| 5,037,427 | 8/1991 | Harada et al. | 606/108 |
| 5,043,632 | 8/1991 | Asars et al. | 315/169.3 |
| 5,043,715 | 8/1991 | Kun et al. | 340/781 |
| 5,057,106 | 10/1991 | Kasevich et al. | 606/33 |
| 5,087,236 | 2/1992 | Morimoto | 493/342 |
| 5,087,256 | 2/1992 | Taylor et al. | 606/28 |
| 5,102,401 | 4/1992 | Lambert et al. | 604/264 |
| 5,102,402 | 4/1992 | Dror et al. | 604/265 |
| 5,104,403 | 4/1992 | Brotzu et al. | 623/1 |
| 5,106,455 | 4/1992 | Jacobsen et al. | 156/659.1 |
| 5,106,627 | 4/1992 | Aebischer et al. | 424/424 |
| 5,108,407 | 4/1992 | Geremia et al. | 606/108 |
| 5,108,420 | 4/1992 | Marks | 606/213 |
| 5,116,345 | 5/1992 | Jewell et al. | 606/130 |
| 5,120,322 | 6/1992 | Davis et al. | 604/265 |
| 5,122,136 | 6/1992 | Guglielmi et al. | 606/32 |
| 5,125,888 | 6/1992 | Howard et al. | 600/12 |
| 5,131,392 | 7/1992 | Jolesz et al. | 128/653.2 |
| 5,133,733 | 7/1992 | Rasmussen et al. | 606/200 |
| 5,138,347 | 8/1992 | Kun et al. | 346/155 |
| 5,154,179 * | 10/1992 | Ratner | 128/653.4 |
| 5,158,548 | 10/1992 | Lau et al. | 604/96 |
| 5,167,625 | 12/1992 | Jacobsen et al. | 604/891.1 |
| 5,171,217 | 12/1992 | March et al. | 604/53 |
| 5,177,441 | 1/1993 | Morich et al. | 324/318 |
| 5,211,165 | 5/1993 | Dumoulin et al. | 128/653.1 |
| 5,211,166 | 5/1993 | Sepponen | 128/653.5 |
| 5,216,366 | 6/1993 | Young | 324/307 |
| 5,217,483 | 6/1993 | Tower | 606/198 |
| 5,221,261 | 6/1993 | Termin et al. | 604/104 |
| 5,226,902 | 7/1993 | Bae et al. | 604/892.1 |
| 5,227,726 | 7/1993 | Young | 324/309 |
| 5,234,456 | 8/1993 | Silvestrini | 606/194 |
| 5,234,457 | 8/1993 | Andersen | 606/198 |
| 5,250,071 | 10/1993 | Palermo | 606/198 |
| 5,258,020 | 11/1993 | Froix | 623/1 |
| 5,263,963 | 11/1993 | Garrison et al. | 606/198 |
| 5,269,882 | 12/1993 | Jacobsen | 156/659.1 |
| 5,270,485 | 12/1993 | Jacobsen | 174/15.1 |
| 5,271,400 | 12/1993 | Dumoulin et al. | 128/653.2 |
| 5,273,622 | 12/1993 | Jacobsen | 156/659.1 |
| 5,303,707 | 4/1994 | Young | 128/653.2 |
| 5,304,194 | 4/1994 | Chee et al. | 606/191 |
| 5,304,197 | 4/1994 | Pinchuk et al. | 606/194 |
| 5,304,199 | 4/1994 | Myers | 606/194 |
| 5,307,813 | 5/1994 | Young | 128/653.4 |
| 5,330,500 | 7/1994 | Song et al. | 606/198 |
| 5,332,625 | 7/1994 | Dunn et al. | 428/409 |
| 5,334,210 | 8/1994 | Gianturco | 606/151 |
| 5,342,303 | 8/1994 | Ghaerzadeh | 604/96 |
| 5,368,566 | 11/1994 | Crocker | 604/101 |
| 5,370,691 | 12/1994 | Samson | 623/12 |
| 5,375,596 | 12/1994 | Twiss et al. | 128/653.1 |
| 5,378,239 | 1/1995 | Termin et al. | 604/104 |
| 5,382,260 | 1/1995 | Dormandy et al. | 606/151 |
| 5,382,261 | 1/1995 | Palmaz | 606/158 |
| 5,382,903 | 1/1995 | Young | 324/318 |
| 5,383,928 | 1/1995 | Scott et al. | 623/1 |
| 5,387,410 * | 2/1995 | Bosworth et al. | 434/9 |
| 5,389,195 | 2/1995 | Ouderkirk et al. | 156/643 |
| 5,409,003 | 4/1995 | Young | 128/653.2 |
| 5,415,163 | 5/1995 | Harms et al. | 128/653.2 |
| 5,441,481 * | 8/1995 | Mishra et al. | 604/29 |
| 5,447,154 | 9/1995 | Cinguin et al. | 128/653.1 |
| 5,451,774 | 9/1995 | Jacobsen | 250/227.24 |
| 5,459,769 | 10/1995 | Brown | 378/4 |

| | | | |
|---|---|---|---|
| 5,470,307 | 11/1995 | Lindall | 604/20 |
| 5,487,739 | 1/1996 | Aebischer et al. | 604/890.1 |
| 5,492,534 * | 2/1996 | Athayde et al. | 604/141 |
| 5,514,092 | 5/1996 | Forman et al. | 604/101 |
| 5,517,993 * | 5/1996 | Unger et al. | 6/173 |
| 5,528,651 | 6/1996 | Leksell et al. | 378/65 |
| 5,534,779 | 7/1996 | Young et al. | 324/319 |
| 5,560,360 * | 10/1996 | Filler et al. | 128/653.2 |
| 5,569,197 | 10/1996 | Helmus et al. | 604/96 |
| 5,571,089 | 11/1996 | Crocker | 604/102 |
| 5,573,668 | 11/1996 | Grosh et al. | 210/490 |
| 5,580,575 | 12/1996 | Unger et al. | 424/450 |
| 5,590,654 | 1/1997 | Prince | 128/653.4 |
| 5,607,418 | 3/1997 | Arzbaecher | 604/891.1 |
| 5,611,025 | 3/1997 | Lorensen et al. | 395/119 |
| 5,612,728 | 3/1997 | Kun et al. | 347/232 |
| 5,628,730 | 5/1997 | Shapland et al. | 604/21 |
| 5,629,967 | 5/1997 | Leksell et al. | 378/65 |
| 5,646,185 | 7/1997 | Giaccia et al. | 514/548 |
| 5,647,361 | 7/1997 | Damadian | 128/683.2 |
| 5,654,864 | 8/1997 | Ritter et al. | 361/141 |
| 5,675,256 | 10/1997 | Young | 324/320 |
| 5,689,189 | 11/1997 | Morich et al. | 324/318 |
| 5,702,372 | 12/1997 | Nelson | 604/264 |
| 5,706,806 * | 1/1998 | Kissinger | 600/309 |
| 5,707,335 | 1/1998 | Howard et al. | 600/12 |
| 5,713,358 | 2/1998 | Mistretta et al. | 128/653.2 |
| 5,713,359 | 2/1998 | Dumoulin et al. | 128/653.2 |
| 5,720,720 | 2/1998 | Laske et al. | 604/49 |
| 5,728,079 * | 3/1998 | Weber et al. | 604/280 |
| 5,741,248 | 4/1998 | Stern et al. | 606/21 |
| 5,744,958 * | 4/1998 | Werne | 324/318 |
| 5,746,208 * | 5/1998 | Prince | 600/420 |
| 5,779,694 * | 7/1998 | Howard et al. | 604/891.1 |
| 5,782,764 | 7/1998 | Werne | 600/411 |
| 5,788,713 * | 8/1998 | Dubach et al. | 606/130 |
| 5,792,110 * | 8/1998 | Cunningham | 604/158 |
| 5,800,392 | 9/1998 | Racchini | 604/96 |
| 5,800,408 | 9/1998 | Strauss et al. | 604/264 |
| 5,840,701 | 11/1998 | Hsia | 514/21 |
| 5,861,175 | 1/1999 | Walters et al. | 424/486 |
| 5,868,674 | 2/1999 | Glowinski et al. | 600/410 |
| 5,908,407 * | 6/1999 | Frazee et al. | 604/101 |
| 5,964,705 | 10/1999 | Truwit et al. | 600/423 |
| 6,026,316 * | 2/2000 | Kucharczyk et al. | 600/420 |

FOREIGN PATENT DOCUMENTS

| | | | |
|---|---|---|---|
| 93/15872 | 8/1993 | (WO) | B23P/17/00 |
| 94/27697 | 12/1994 | (WO) | A65M/25/00 |
| 96/33761 | 10/1996 | (WO) | A61M/25/00 |

OTHER PUBLICATIONS

Dubach, M., "Accurate stereotaxic injection by radially curved injection needle", *Neurosurgery*, 29 (1), 144–149, (Jul. 1991).

Gillies, G., et al., "Magnetic Manipulation Instrumentation for Medical Physics Research", *Review of Scientific Instruments*, 65 (3), 533–562, (Mar. 1994).

Grady, M., et al., "Magnetic Stereotaxis: A Technique to Deliver Stereotactic Hyperthermia", *Neurosurgery*, 27, (6), 1010–1016, (Dec. 1990).

Grady, M., et al., "Nonlinear Magnetic Stereotaxis: Three–Dimensional, in vivo Remote Magnetic Manipulation of a Small Object in Canine Brain", *Medical Physics*,17 (3), AAPM Annual Meeting Issue, St. Louis, MO, 405–415, (May/Jun. 1990).

Grady, M., et al., "Preliminary Experimental Investigation of in vivo Magnetic Manipulation: Results and Potential Application in Hyperthermia", *Medical Physics*, 16 (2), 263–272, (Mar./Apr. 1989).

Hajnal, J.V., et al., "MR Imaging of Anisotropically Restricted Diffusion of Water in the Nervous System: Technical, Anatomic, and Pathologic Considerations", *Journal of Computer Assisted Tomography*, 15 (1), 1–18, (Jan./Feb. 1991).

Hasegawa, Y., et al., "Temperature dependent change of apparent diffusion coefficient of water in normal and ischemic brain of rats", *Journal of Cereberal Blood Flow and Metabolism*, 14 (3), 383–390, (1994).

Hilal, S.K., et al., "Magnetically guided devices for vascular exploration and treatment", *Radiology*, 113 (3), 529–540, (Dec. 1974).

Hilal, S.K., et al., "POD Catheter: A Means for Small Vessel Exploration", *Abstract, Journal of Applied Physics 40 (3)*, (Mar. 1, 1969).

Howard, M., et al., "Magnetic Movement of a Brain Thermoceptor", *Neurosurgery*, 24 (3), 444–448, (1989).

Howard, M.A., "Stereotaxic pallidotomy for the treatment of Parkinson's Disease", *Current Surgery*, 54 (1), 31–34, (Jan. 1997).

Howard, M.A., et al., "An integrated multipurpose lesion–making electrode", *Neurosurgery*, 42 (1), 137–142, (Jan. 1998).

Howard, M.A., et al., "Magnetically guided stereotaxis", *Advanced Neurosurgical Navigation*, Chapter 45, 549–556, (1999).

Hurst, G.C., et al., "Intravascular (Catheter) NMR Receiver Probe: Preliminary Design Analysis and Application to Canine Iliofemoral Imaging", *Magnetic Resonance in Medicine 24 (2)*, 343–357, (Apr. 1992).

Johnston, J., et al., "Shiley Infusaid Pump Technology", *Annals of the New York Academy of Sciences 531*, Neurological Applications of Implanted Drug Pumps, 57–65, (1988).

Kucharczyk, J., et al., "Differential Effects of Brain Lesions on Thirst Induced by the Administration of Angiotensin–II to the Preoptic Region, Subfornical Organ and Anterior Third Ventricle", *Brain Research*, 108, 327–337, (1976).

Laske, D.W., et al., "Chronic Interstital Infusion of Protein to Primate Brain: Determination of Drug Distribution and Clearance with Single–Photon Emission Computerized Tomography Imaging", *Journal of Neurosurgery 87 (4)*, 586–594, (Oct. 1997).

Lieberman, D.M., et al., "Convection–enhanced distribution of large molecules in gray matter during interstitial drug infusion", *Journal of Neurosurg*, 82 (6), 1021–1029, (Jun. 1995).

Lux, H.D., et al., "The equilibration time course of (K+)o in cat cortex", *Experimental Brain Research*, 17 (2), 190–205, (Apr. 30, 1973).

Martin, A.J., et al., "MR Imaging of Blood Vessels with an Intravascular Coil", *Journal of Magnetic Resonance Imaging 2 (4)*, 421–429, (Jul./Aug. 1992).

Basser, P.J., "Interstitial Pressure, Volume, and Flow during Infusion into Brain Tissue", *Microvascular Research 44 (2)*, 143–165, (Sep. 1992).

Bouvier, G., et al., "Direct Delivery of Medication into a Brain Tumor through Multiple Chronically Implanted Catheters", *Neurosurgery*, 20 (2), 286–291, (Feb. 1987).

Broaddus, W.C., et al., "Distribution and stability of antisense phosphorothioate oligonucleotides in rodent brain following direct intraparenchymal controlled–rate infusion", *Journal of Neurosurgery*, 88 (4), 734–742, (Apr. 1998).

McNeil, R., et al., "Characteristics of an Improved Magnetic–Implant Guidance System", *IEEE Transactions on Biomedical Engineering*, 42 (8), 802–808, (Aug. 1995).

McNeil, R., et al., "Functional Design Features and Initial Performance Characteristics of a Magnetic–Implant Guidance for Stereotactic Neurosurgery", *IEEE Transactions on Biomedical Engineering*, 42 (8), 793–801, (Aug. 1995).

Meeker, D., et al., "Optimal Realization of Arbitrary Forces in a Magnetic Stereotaxis System", *IEEE Transactions on Magnetics*, 32 (2), 320–328, (Mar. 1996).

Molcho, J., et al., "Selective cerebral catheterization", *IEEE-Transsctions on Biomedical Engineering*, 17 (2), 134–140, (Apr. 1970).

Molloy, J., et al., "Experimental Determination of the Force Required for Insertion of a Thermoseed into Deep Brain Tissues", *Annals of Biomedical Engineering*, 18, 299–313, (1990).

Molloy, J., et al., "Thermodynamics of Movable Inductively Heated Seeds for Treatment of Brain Tumors", *Medical Physics*, 18 (4), 794–803, (Jul./Aug. 1991).

Morrison, P.F., et al., "High–flow microinfusion: tissue penetration and pharmacodynamics", *American Journal of Physiology*, 266 (1) Part 2 of 2 Parts, R292–R305, (Jan. 1994).

Moseley, M.E., et al., "Anisotrophy in diffusion–weighted MRL", *Magnetic Resonance in Medicine*, 19 (2), 321–326, (Jun. 1991).

Moseley, M.E., et al., "Magnetic resonance imaging of diffusion and perfusion", *Topics in Magnetic Resonance Imaging*, 3 (3), Magnetic resonance Angiography, 50–67, (Jun. 1991).

Netti, P.A., et al., "Time–dependent behavior of interstitial fluid pressure in solid tumors: implications for drug delivery", *Cancer Research*, 55 (22), 5451–5458, (Nov. 15, 1995).

Nicholson, C., et al., "Diffusion from and iontophoretic point source in the brain: role of tortuosity and volume fraction", *Brain Research*, 169 (3), 580–584, (Jun. 29, 1979).

Nicholson, C., et al., "Hindered diffusion of high molecular weight compounds in brain extracellular microenvironment measured with integrative optical imaging", *Biophysical Journal*, 65 (6), 2277–2290, (Dec. 1993).

Nicholson, C., et al., "Ion diffusion modified by tortuosity and volume fraction in the extracellular microenviroment of the rat cerebellum", *The Journal of Physiology*, 321, 225–257, (1981).

Oldendorf, W.H., "Speculations on the Instrumentation of the Nervous System", *Proceedings of the San Diego Symposium for Biomedical Engineering* , 2, San Diego, CA, 274–280, (Jun. 19–21, 1962).

Penn, R.D., et al., "Intravascular intracranial EEG recording. Technical note", *Journal of Neurosurgery*, 38 (2), 239–243, (Feb. 1973).

Prabhu, S.S., et al., "Distrubution of macromolecular dyes in brain using positive pressure infusion: a model for direct controlled delivery of therapeutic agents", *Surgical Neurology*, 50 (4), 367–375, (Oct. 1998).

Quate, E., et al., "Goniometric Motion Controller for the Superconducting Coil in a Magnetic Stereotaxis System", *IEEE Transactions on Biomedical Engineering*, 38 (9), 899–905, (Sep. 1991).

Ram, W., et al., "Heart catheterization in a neonate by interacting magnetic fields: a new and simple method of catheter guidance", *Catheterization and Cardiovascular Diagnosis*, 22 (4), 317–319, (Apr. 1991).

Ramos, P., et al., "Electro–Optic Imaging Chain for a Biplanar Fluoroscope for Neurosurgery: Magnetic Field Sensitivity and Contrast Measurements", *Optical Engineering 32 (7)*, 1644–1656, (Jul. 1993).

Ramos, P., et al., "Microchannel Plate Image Intensifier Electron Dynamics in Magnetic Field", *Electronics Letters*, 27 (18), 1636–1638, (Aug. 29, 1991).

Ritter, R.C., et al., "Measurment of friction on straight catheters in in vitro brain and phantom material", *IEEE Transactions on Biomedical Engineering*, 45 (4), 476–485, (Apr. 1998).

Schmitt, F.O., "Molecular Regulators of Brain function: A New View", *Neuroscience*, 13 (4), 991–1001, (1984).

Sendelbeck, S.L., et al., "Spatial Distribution of Dopamine, Methotrexate and Antipyrine During Continuous Intracerebral Microperfusion", *Brain Research*, 328 (2), 251–258, (Mar. 4, 1985).

Swanson, L.W., et al., "Autoradiographic Evidence for Pathways from the Medial Preoptic Area to the Midbrain Involved in the Drinking Response to Angiotensin II", *Journal of Comparative Neurology*, 178 (4), 645–659, (Apr. 15, 1978).

Wimberger, D.M., et al., "Identification of "Premyelination" by Diffusion–Weighted MRI", *Journal of Computer Assisted Tomography*, 19 (1), 28–33, (1995).

* cited by examiner

MR-VISIBLE MEDICAL DEVICE FOR NEUROLOGICAL INTERVENTIONS USING NONLINEAR MAGNETIC STEREOTAXIS AND A METHOD IMAGING

BACKGROUND OF THE INVENTION

1. Field of the Invention

The present invention relates to a method of delivery of medical devices to patients, especially a method where (e.g., neurological) devices are delivered using nonlinear magnetic stereotaxis in conjunction with non-invasive MR imaging observation techniques such as magnetic resonance imaging, and most especially where drug delivery by said devices is accomplished under real time, non-invasive observation techniques such as magnetic resonance imaging which can indicate metabolic responses to the delivered drug and/or changes in soluble/dispersed concentrations of materials within liquids and/or tissue of a patient in real time or near real time.

2. Background of the Prior Art

The concept of admninistering minimally invasive therapy and especially minimally invasive drug delivered therapy follows recent trends in medical and surgical practice towards increasing simplicity, safety, and therapeutic effectiveness. Image-guided, minimally invasive therapies have already superseded conventional surgical methods in several procedures. For example, transvascular coronary angioplasty is often now an alternative to open-heart surgery for coronary artery bypass, and laparascopic cholecystectomy is often an alternative to major abdominal surgery for gall bladder removal. The use of the less invasive techniques has typically reduced hospital stays by 1–2 weeks and the convalescence periods from 1–2 months to 1–2 weeks.

While endoscopic, arthroscopic, and endovascular therapies have already produced significant advances in health care, these techniques ultimately suffer from the same limitation. This limitation is that the accuracy of the procedure is "surface limited" by what the surgeon can either see through the device itself or otherwise visualize (as by optical fibers) during the course of the procedure. That is, the visually observable field of operation is quite small and limited to those surfaces (especially external surfaces of biological masses such as organs and other tissue) observable by visible radiation, due to the optical limitations of the viewing mechanism. MR imaging, by comparison, overcomes this limitation by enabling the physician or surgeon to non-invasively visualize tissue planes and structures (either in these planes or passing through them) beyond the surface of the tissue under direct evaluation. Moreover, MR imaging enables differentiation of normal from abnormal tissues, and it can display critical structures such as blood vessels in three dimensions. Prototype high-speed MR imagers which permit continuous real-time visualization of tissues during surgical and endovascular procedures have already been developed. MR-guided minimally invasive therapy is expected to substantially lower patient morbidity because of reduced post-procedure complications and pain. The use of this type of procedure will translate into shorter hospital stays, a reduced convalescence period before return to normal activities, and a generally higher quality of life for patients. The medical benefits and health care cost savings are likely to be very substantial.

A specific area where research is moving forward on advances of this type is in the treatment of neurological disorders. Specifically, the advent of new diagnostic and therapeutic technologies promises to extend the utility of intracerebral drug delivery procedures and thus possibly advance the efficacy of existing and/or planned treatments for various focal neurological disorders, neurovascular diseases and neurodegenerative processes. Currently, when the standard procedure requires neurosurgeons or interventional neuroradiologists to deliver drug therapy into the brain, the drug delivery device, such as a catheter, must either be passed directly through the intrapa-renchymal tissues to the targeted region of the brain, or guided through the vasculature until positioned properly. An important issue in either approach is the accuracy of the navigational process used to direct the movement of the drug delivery device. In many cases, the physical positioning of either part or all of the catheter's lumen within the brain is also important as, for example, in situations where a drug or some other therapeutic agent will be either inflsed or retroperfiised into the brain through the wall or from the tip of the catheter or other drug delivery device.

New technologies like intra-operative magnetic resonance imaging and nonlinear magnetic stereotaxis, the latter discussed by G. T. Gillies, R. C. Ritter, W. C. Broaddus, M. S. Grady, M. A. Howard III, and R. G. McNeil, "Magnetic Manipulation Instrumentation for Medical Physics Research," *Review of Scientific Instruments*, Vol.65, No.3, pp.533–562 (March 1994), as two examples, will likely play increasingly important roles here. In the former case, one type of MR unit is arranged in a "double-donut" configuration, in which the imaging coil is split axially into two components. Imaging studies of the patient are performed with this system while the surgeon is present in the axial gap and carrying out procedures on the patient. A second type of high-speed NMR imaging system combines high-resolution MR imaging with conventional X-ray fluoroscopy and digital subtraction angiography (DSA) capability in a single hybrid unit. These new generations of MR scanners are able to provide the clinician with frequently updated images of the anatomical structures of interest, therefore making it possible to tailor a given interventional procedure to sudden or acute changes in either the anatomical or physiological properties of, e.g., a part of the brain into which a drug agent is being infused.

Nonlinear magnetic stereotaxis is the image-based magnetically guided movement of a small object directly through the bulk brain tissues or along tracts within the neurovasculature or elsewhere within the body. Electromagnets are used to magnetically steer the implant, giving (for example) the neurosurgeon or interventional neuroradiologist the ability to guide the object along a particular path of interest. (The implant might be either magnetically and/or mechanically advanced towards its target, but is magnetically steered, in either case. That is, magnetic fields and gradients are used to provide torques and linear forces to orient or shift the position of the implant or device, with a mechanical pushing force subsequently providing none, some, or all of the force that actually propels the implant or device. Additional force may be provided magnetically.) The implant's position is monitored by bi-planar fluoroscopy, and its location is indicated on a computerized atlas of brain images derived from a preoperative MR scan. Among other applications, the implant might be used to tow a pliable catheter or other drug delivery device to a selected intracranial location through the brain parenchyma or via the neurovasculature. Magnetic manipulation of catheters and other probes is well documented in research literature. For example, Cares et al. (J. Neurosurg, 38:145, 1973) have described a magnetically guided microballoon released by RF induction heating, which was used to occlude experimental intracranial aneurysms. More recently, Kusunoki et al. (Neuroradiol 24: 127, 1982) described a magnetically controlled catheter with cranial balloon useful in treating experimental canine aneurysms. Ram and Meyer (Cathet. Cardiovas. Diag.22:317, 1991) have described a permanent magnet-tipped polyurethane angiography catheter useful in cardiac interventions, in particular intraventricular catheterization in neonates.

U.S. Pat. No. 4,869,247 teaches the general method of intra parenchymal and other types of magnetic manipulation, and U.S. Pat. Nos. 5,125,888; 5,707,335; and 5,779,694 describe the use of nonlinear magnetic stereotaxis to maneuver a drug or other therapy delivery catheter system within the brain. U.S. Pat. No. 5,654,864 teaches a general method of controlling the operation of the multiple coils of a magnetic stereotaxis system for the purpose of maneuvering an implant to precisely specified locations within the body.

Both of these technologies offer a capability for performing image-guided placement of a catheter or other drug delivery device, thus allowing drug delivery directly into the brain via infusion through the walls of the catheter or out flow of the tip off the catheter. In the case of drug delivery directly into the brain tissues, the screening of large molecular weight substances by the endothelial blood-brain barrier can be overcome. In the case of infusions into specific parts of the cerebrovasculature, highly selective catheterizations can be enabled by these techniques. In either case, however, detailed visual images denoting the actual position of the drug delivery device within the brain would be extremely useful to the clinician in maximizing the safety and efficacy of the procedure. The availability of an MR-visible drug delivery device combined with MR-visible drug agents would make it possible to obtain near real-time information on drug delivery during interventional procedures guided by non-linear magnetic stereotaxis. Drug delivery devices, such as catheters, that are both MR-visible and radio-opaque could be monitored by two modalities of imaging, thus making intra-operative verification of catheter location possible during nonlinear magnetic stereotaxis procedures. (Intra-operative MR assessment might require the temporary removal of the magnetic tip of the drug delivery catheter and interruption of the magnetic stereotaxis procedure to image the patient.).

The geometry and magnetic strength of the magnetic tip will depend upon the particular type of catheter or medical device with which the tip is being used. In a preferred embodiment, the tip would have as small a maximum dimension as would be consistent with maintaining sufficient magnetic dipole moment to couple satisfactorily to the external magnetic fields and gradients used to apply torques and forces to the tip for the purpose of steering or moving the catheter or other medical device. It is preferred that the magnetic element (e.g., a distinct magnetic bead or seed or wire) or the magnetic tip have a maximum dimension of at least 0.5 mm, preferably from 0.5 to 8 mm, more preferably from about 1.0 to 6 mm, and most preferably from about 2 to 5 or 6 mm. To that end, the tip might be made of a permanently magnetic or magnetically permeable material, with compounds of Nd—B—Fe being exemplary, as well as various iron alloys (ferrites and steel alloys). The magnetic tip may be fixed to the disttl end of the catheter in any number of ways, depending in part upon the method of use of the catheter, the specific type of catheter, the procedures and the use of the catheter. In one design, the magnetic tip might simply be a small spherical or oblate spheroid of magnetic material (e.g., having a geometry where the semi-major axis is from 1.1 to 3 times longer, preferably from 1.5 to 2.0 or 2.5 time longer than the semi-minor axis). The magnetic tip may be originally fixed to the distal end of the catheter or medical device or passed through the length of the catheter so that it abuts against the interal distal end of the catheter (as a foot would abut the end of a sock). As noted, the magnetic tip may be fixed in place either on the inside, outside or embedded within the composition of the distal end of the catheter or medical device. In a preferred embodiment, the magnetic tip may be thermally, solubly, mechanically, electronically or otherwise removably attached to and separable from the distal end of the catheter or medical device. A heat soluble link is taught in U.S. Pat. No. 5,125,888.

In still another embodiment, the magnetic tip would constitute a plug in the end of an otherwise open-ended catheter, and the tip might either have an open bore along its axis, a plurality of open bores along its axis, or a single or plural configuration of holes along the side of the magnetic tip, any of which openings would be used to facilitate drug delivery from the catheter or to serve as an exit port for the delivery of some other therapy or device into a body part, such as the parenchymal tissues and/or the cerebrobasculature of the brain. Alternatively, the magnetic tip might simply constitute a solid plug that seals the end of the catheter. The distal end of the catheter at which the magnetic tip is placed must be configured such that axial forces and torques applied by either magnetic fields and gradients or by a guide wire internal to the catheter allow said distal end and magnetic tip to be propelled towards a target site with the body, and to do so without said distal end and magnetic tip separating from each other in an inappropriate way and/or at an undesired time or under undesired circumstances. If the magnetic tip must be removed, or detached and removed, prior to MR imaging of the patient, such a procedure could be accomplished by the method taught in U.S. Pat. Nos. 5,125,888; 5,707,335; and 5,779,694, which call for dissolving a heat separable link between the tip and the catheter by a pulse of radio-frequency energy. An alternative means of removing the magnetic tip is discussed by M. A. Howard et al. in their article, "Magnetically Guided Stereotaxis," in Advanced Neurosurgical Navigation, edited by E. Alexander III and R. J. Maciunas (Thieme Medical Publisher, New York, 1998), which calls for withdrawing the magnetic tip from along the inside of the catheter that it has just steered into place within the body. Without removal of the magnetic tip from the catheter, whole body magnetic forces might be produced on it by the field of the MR imaging system, and these could cause undesired movement of the catheter that it has just steered into place within the body.

In the treatment of neurological diseases and disorders, targeted drug delivery can significantly improve therapeutic efficacy, while minimizing systemic side-effects of the drug therapy. Image-guided placement of the tip of a drug delivery catheter directly into specific regions of the brain can initially produce maximal drug concentration-close to some targeted loci of tissue receptors following delivery of the drug. At the same time, the limited distribution of drug injected from a single catheter tip presents other problems. For example, the volume flow rate of drug delivery must be very low to avoid indiscriminate hydrodynamic damage or other damage to brain cells and nerve fibers. Delivery of a drug from a single point source may also limit the distribution of the drug by decreasing the effective radius of penetration of the drug agent into the surrounding tissue receptor population. Positive pressure infusion, i.e., convection-enhanced delivery of drugs into the brain, as taught by U.S. Pat. No. 5,720,720 may overcome the problem of effective radius of penetration. Also, U.S. patent application Ser. No. 08/857,043, filed on May 15, 1997 and titled "Method and Apparatus for Use with MR Imaging" describes a technology invented in-part by one of the present inventors comprising a method for observing the delivery of material to tissue in a living patient comprising the steps of a) observing by magnetic resonance imaging a visible image within an area or volume comprising tissue of said living patient, the area or volume including a material delivery device, b) delivering at least some material by the material delivery device into the area or volume comprising tissue of a living patient, and c) observing a change in property of said visible image of the area or volume comprising tissue of a living patient while said material delivery device is still present within the area or volume. This process, including the MRI visualization, is performed in approximately or actually real time, with the clinical procedure being guided by the MRI visualization.

Research on magnetic catheterization of cerebral blood vessels generally has focused on design of transvascular devices to thrombose aneurysms, to deliver cytotoxic drugs to tumors, and to deliver other therapies without the risks of major invasive surgery. Examples of such studies include Hilal et al (J.Appl. Phys. 40:1046, 1969), Molcho et al (IEEE Trans. Biomed. Eng. BME-17, 134, 1970), Penn et al (J. Neurosurg. 38:239, 1973), and Hilal et al (Radiology 113:529,1974).

U.S. Pat. Nos. 4,869,247, 5,654,864, 5,125,888, 5,707, 335 and 5,779,694 describe processes and apparatus for the use of magnetic stereotaxis for the manipulation of an object or implant which is moved into position within a patient, particularly within the cranial region and specifically within the brain but in principle elsewhere in the body also. These patents do no not involve any contemplation of real time visualization of drug distribution within the brain, especially by MRI. It should be noted that the potential exists for interactive interference between the two systems, magnetic resonance imaging and magnetic stereotaxis, particularly where fine images are being provided by a system based on magnetic coils, especially as described in U.S. patent application Ser. No. 08/916,596, filed on Aug. 22, 1997, which is incorporated herein by reference for its disclosure of the design, construction, structure and operation of coils and catheters in MR-guided procedures.

A source of drug delivery can be effected by devising a multi-lumen catheter with multiple drug release sources that effectively disperse therapeutic drug agents over a brain region containing receptors for the drug, or over an anatomically extensive area of brain pathology. A preferred type of structure is described in U.S. patent application Ser. No. 08/916,596, filed on Aug. 22, 1997, but other devices which are described in the background of the art in that application could also be used in the practice of the present invention.

It should be noted that the potential exists for interactive interference between the two systems, i.e., magnetic resonance imaging and magnetic stereotaxis. This is because both modalities rely on the creation of large external magnetic fields to function as designed. The magnetic field and field gradients of the magnetic stereotaxis system are used to steer an implant within the body, and especially within the brain, while the magnetic fields of the magnetic resonance imager are used to create images of the planes of tissue within the patient's body. The magnetic fields of either one of these systems/devices can perturb the size and shape (and, therefore, the function) of the fields of the other device. It is unlikely that a clinical configuration of these systems/ devices would be purposely arranged so as to cause direct interference via interaction of the fields. However, a far more likely danger is that the magnetic tip of the implanted catheter or other MSS-guided device will experience bulk-body forces and torques if the patient is placed in the MR and is subjected to the resulting magnetic field produced during the course of its functioning. Such a field could very easily cause the magnetically-tipped implant to move away from the location into which it was navigated by the clinician operating the magnetic sterotaxis system. This might produce a dangerous situation for the patient and, hence, care must be taken to insure that the magnetic tip is either removed from the catheter in the patient prior to MR imaging, or that it is otherwise deactivated or made impervious to the effects of non-MSS fields to which it might be subjected. Moreover, the presence of a relatively large magnetic dipole in the patient's body, as might arise from the presence of the magnetic tip of the implanted catheter, would create artifacts in the MR images.

SUMMARY OF THE INVENTION

This invention provides a method and object for selective intraparenchymal and/or neuroendovascular drug delivery and other concurrent medical treatment of abnormalities of the human central nervous system concurrent with nonlinear magnetic stereotaxis combined with magnetic resonance (MR) imaging and/or x-ray guidance.

Magnetic Resonance Imaging (MRI) is used in combination with 1) an MR observable delivery device or 2) an MR observable medical device which can alter a water based molecular environment by performed medical operations, the delivery device or medical device being used in the presence of MR observable (in water, body fluid or tissue) compound(s) or composition(s). MRI images are viewed with respect to a molecular environment to determine the position of the delivery device or medical device (hereinafter collectively referred to as the "delivery device" unless otherwise specifically identified) and changes in the environment where the delivery device is present as an indication of changes in the molecular environment. As the delivery of material from the delivery device is the most MR visible event within the molecular environment in the vicinity of the delivery area, the changes in the molecular environment are attributable to the delivery of the MR observable compounds or compositions. Changes in signal properties, such as changes in the signal intensity within the MR images reflect the changes in the molecular environment and therefore track the location of delivered materials, and are indicative of delivery rates and delivery volumes in viewable locations. With the medical device, chemical composition within the molecular environment may also be altered as by the removal of deposits of certain materials into the liquid (water) environment or stimulated activity of tissue to release materials, where those materials can alter the MR response. Some materials that may be removed by medical procedures will not affect the MR response, such as calcium, but fatty materials may affect the response. Additionally, medical treatments which stimulate natural activities of chemical producing systems (e.g., the glands, organs and cells of the body which generate chemicals such as enzymes and other chemicals with specific biological activity [e.g., dopamine, insulin, etc.]) can be viewed under direct MR observation and any changes in chemical synthetic activity and/or delivery can be observed because of molecular environment changes which occur upon increased synthetic activity.

One recently established method of reading the data obtained from the MR imaging is technically founded upon existing knowledge of Apparent Diffusion Coefficients (ADC) in particular regions of the body. There is significant published literature with respect to ADC values for specific tissues in various parts of animals, including various tissues of humans (e.g., Joseph V. Hajnal, Mark Doran, et al., "MR Imaging of Anisotropically Restricted Difflusion of Water in the Nervous System: Technical, Anatomic, and Pathological Considerations," Journal of Computer Assisted Tomography, 15(1): 1–18, January/February, 1991, pp. 1–18). It is also well established in the literature that loss of tissue structure through disease results in a decrease of the ADC, as the tissue becomes more like a homogeneous suspension. Clinical observations of changes in diffusion behavior have been made in various tissue cancers, multiple sclerosis, in strokes (where the reduction in diffusion precedes the increase in T2), and in epilepsy. (e.g., Y. Hasegawa, L. Latour, et al. "Temperature Dependent Change of Apparent Diffuision Coefficient of Water in Normal Ischemic Brain", Journal of Cerebral Blood Flow and Metabolism 14:389–390, 1994). Thus, ADC values are specific for specific types of tissues. Accordingly, as different drugs/chemicals are introduced into a tissue volume under MR observation, the change in ADC resulting from each drug/chemical interaction with the ambient water proton environment can be observed.

While the ADC is the preferred means within the present invention of mapping the delivery of drug in tissue, other embodiments of the invention allow for additional tissue contrast parameters to track the delivery of a drug into tissue. In other words, the delivery of a drug into tissue will cause other MRI-observable changes which can be mapped (as is done for ADC) and which can be used to map the spatial distribution characteristics of the drug within and around the targeted tissue. While some of these-observations may be larger in magnitude than others, any of the MRI contrast mechanisms effects can be used as a tracking mechanism to longitudinally evaluate the spatial kinetics of drug movement within the imaging volume.

The tissue contrast changes apparent on an MR image can arise from ADC, from alterations in the BO magnetic field (often referred to as magnetic susceptibility or ABO produced by the presence of a substance in said tissue), from alterations in local tissue T1 relaxation times, from local T2 relaxation times, from T2* relaxation times (which can be created by susceptibility differences), from the magnetization transfer coefficients (MTC is an effect produced by local communication between free water protons and those of nearby macromolecular structures), from the ADC anisotropy observed in oriented matter, and also from local differences in temperature which will affect in varying degrees all of the included tissue contrast parameters. In addition, the delivery of drug can also be tracked from magnetic field frequency shifts caused by the drug or arising from agents (e.g., MR taggants) added with unique frequency shifts from those of the local protons (such as that created from F-19 or fluorine-19 agents found in or added to the drug).

MR imaging of the alterations in the BO magnetic field (also known as imaging of the local magnetic susceptibility) can reveal the spatial distribution of a drug from the interaction of the drug with the otherwise homogeneous magnetic field found in MRI. To enhance the alterations in the magnetic field BO caused by the drug, small amounts of a BO-altering added agent or agents can be added to the drug during delivery. This can include iron oxide particles, or other materials, such as those comprising lanthanide-, manganese-, and iron-chelates. In addition, vehicles containing differing gases ($N_2$, $O_2$, $CO_2$) will also alter the local magnetic field and thus produce a magnetic susceptibility effect which can be imaged.

The invention includes a device for use in conjunction with magnetic stereotaxis guidance and device delivery and a method for MR-guided targeted drug delivery into a patient, such as intracranial drug delivery, intraspinal drug delivery, intrarenal drug delivery, intracardial drug delivery, etc. The MR-visible drug delivery device is guided by magnetic stereotaxis to the target tissue and/or advanced within entrance points to the patient such as periventricular, intracerebroventricular, subarachnoid, intraparenchymal tissues or the cerebrovasculature under magnetic resonance imaging or real time X-ray fluoroscopy, and all of this is possibly also done in conjunction with conventional methods of neurosurgical or neuroradiologic catheter manipulation. The drug delivery device preferably has a linearly arranged array of radiopaque and MR-visible markers disposed at its distal end to provide easily identifiable reference points for trackability and localization under susceptibility MR imaging and X-ray fluoroscopy guidance. Additionally, active MR visualization of the drug delivery device is achieved or enhanced by means of RF microcoils positioned along the distal axis of the device. MR visibility can be variably adjustable based on requirements related to degree of signal intensity change for device localization and positioning, enhancement along the shaft of the device, enhancement around the body of the device, visibility of the proximal and distal ends of the device, degree of increased background noise associated with device movement, and other factors which either increase or suppress background noise associated with the device. Since the tip of the drug delivery device can be seen on MR and X-ray images and thus localized within the brain, the multiple point source locations of drug delivery are therefore known and can be seen relative to the tip or the shaft of the device.

Targeted delivery of drug agents may be performed by any therapeutically effective drug delivery device or system, including, for example, those utilizing MR-compatible pumps connected to variable-length concentric MR-visible dialysis probes each with a variable molecular weight cut-off membrane, or by another MR-compatible infusion device which injects or infuses a diagnostic or therapeutic drug solution. Imaging of the injected or infused drug agent is performed by MR diffusion mapping using the RF microcoils attached to the distal shaft of the injection device, or by imaging an MR-visible contrast agent that is injected or infused through the walls of the dialysis fiber into the brain. The delivery and distribution kinetics of injections or infusions of drug agents at rates, for example, of between 1 $\mu$l/min (or less) to 1000 $\mu$l/min (or more) are monitored quantitatively and non-invasively using real-time contrast-enhanced magnetic susceptibility MR imaging combined with water proton directional diffusion MR imaging. One aspect of the present invention is to provide a non-invasive, radiation-free imaging system for tracking a drug delivery or other medical device to a target intracranial location in conjunction with or following magnetic stereotaxis manipulation and placement of the drug delivery device in the procedure.

Another aspect of the present invention is to provide an imaging system for visualizing the distal tip of the drug delivery or other medical device at the target intracranial location in conjunction with or following magnetic stereotaxis delivery of the drug delivery device in the procedure.

A third aspect of this invention is to provide for an MR-compatible and visible device that significantly improves the efficacy and safety of intracranial drug delivery using MR guidance in conjunction with or following magnetic stereotaxis delivery of the drug delivery device in the procedure.

A fourth aspect of the present invention is to provide for interactive MR imaging of injected or infused MR-visible drug agents superimposed upon diagnostic MR images of the local intracranial anatomy in conjunction with or following magnetic stereotaxis delivery of the drug delivery device and manipulation and placement of the device in the procedure.

A fifth aspect of the present invention is provide an MR imaging method for quantitative monitoring of the spatial distribution kinetics of a drug agent injected or infused from a drug delivery device into the central nervous system or cerebrovascular system to determine the efficacy of drug delivery at various sites, such as at intracranial target sites.

A sixth aspect of the present invention is to provide for magnetically responsive catheters and other drug delivery devices which can be steered by an applied magnetic field using nonlinear magnetic stereotaxis to provide directional control of the tip of the device to guide the device to targeted intracranial locations.

A seventh aspect of this invention is to provide for a magnetically responsive catheter device which can be steered or navigated through bulk tissues in the brain using nonlinear magnetic stereotaxis with minimal frictional drag and minimal tissue injury.

An eighth aspect of this invention is to provide for a magnetically responsive catheter device which can be guided by nonlinear magnetic stereotaxis to sites of cerebrovascular lesions, including aneurysms, stroke sites, tumors, arteriovenous malformations and fistulae.

A ninth aspect of the present invention is to provide an MR imaging method to evaluate how the spatial distribution kinetics of a drug agent injected or infused from a drug delivery device into the central nervous system is influenced by infusion pressure, flow rate, tissue swelling and other material properties of the brain, and by the physicochemical and phannaco kinetics nature of the drug or therapeutic agent infused.

DETAILED DESCRIPTION OF THE INVENTION

Figure 1:
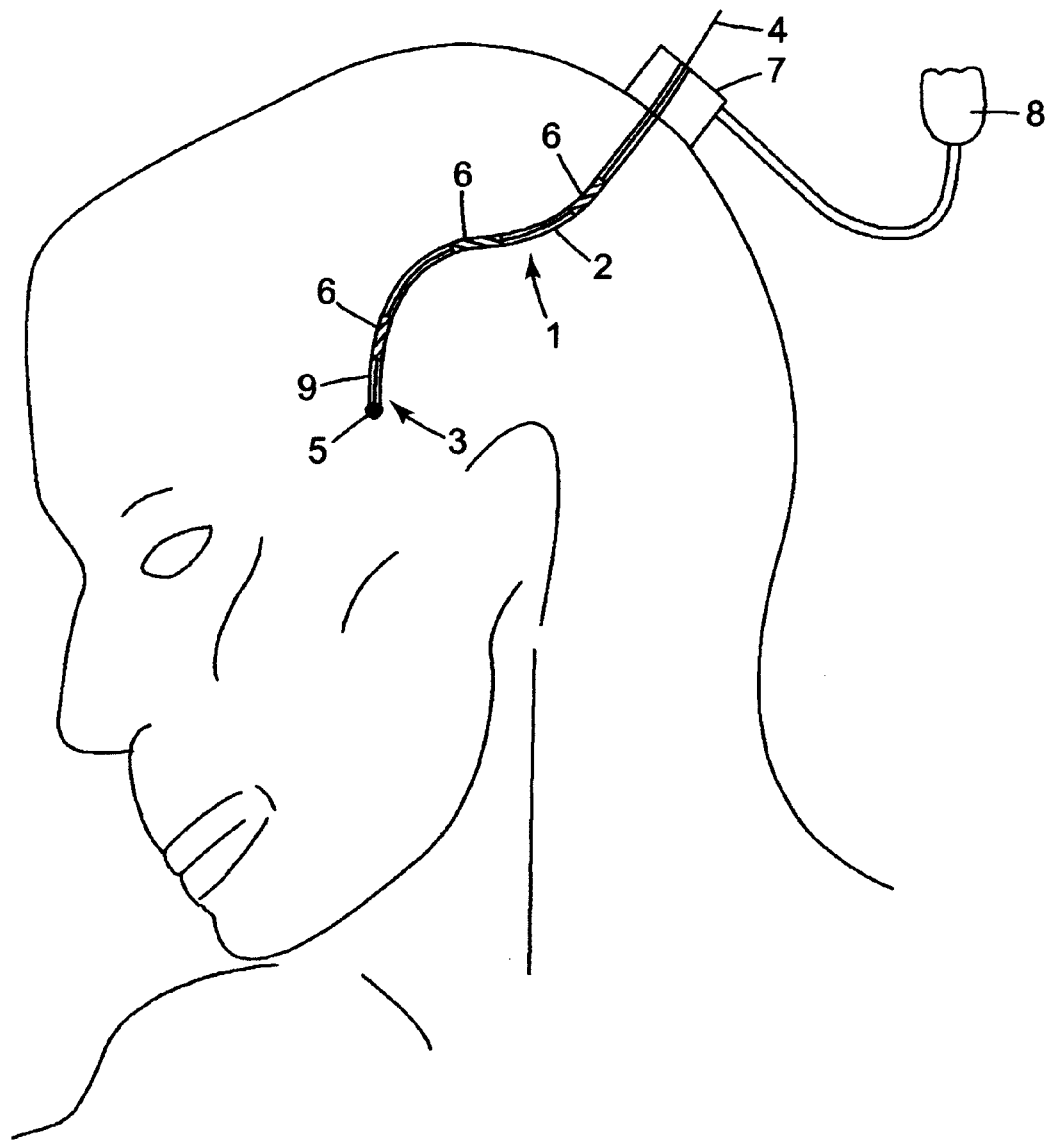
FIG. 1 is a side elevational view, partially in cross-section, of a retroperfusion microcatheter or other drug delivery device which might be used for infusion, retroperfusion or other purposes according to one embodiment of the present invention, that is designed to be maneuvered intracranially via nonlinear magnetic stereotaxis. The view shows the disposition of radio-opaque and MR markers, and the relationship of the osmotic pump and microdialysis probe.

One of the significant difficulties with delivery of materials such as drugs, hormones, or neurotransmitters to living tissue is assuring that the materials are delivered to the target receptor location in the intended amount, and to reduce collateral damage by a) physical impact and/or spurious tissue penetration by delivery devices and b) by cell damage from the potent effects of the drugs themselves. Many materials which are delivered to a patient, even though beneficial in the treatment of a specific condition, may be moderately or even strongly noxious or damaging to healthy tissue. It is therefore one object of conventional materials application treatment to maximize dosage to a desired location and to minimize dosage to locations which do not require the delivery of the material. Additionally, newer medical treatments may include procedures which remove unwanted deposits of materials with an expectation that the removal will be assisted by physical removal (by a withdrawal system) or natural bodily function removal (e.g., dissolution with subsequent transport through the circulatory system). Newer treatments also may attempt to stimulate the body to produce natural chemicals (of which a patient may be deficient) at an increased rate (e.g., electrical stimulation to increase the production of dopamine). Because these procedures are usually highly invasive, it would be extremely desirable to have a real time indication of immediate, transient and persistent effectiveness of the procedure. Where undesired deposits or collections of materials are being dispersed, it would be desirable to visualize the actual movement of materials to assist in collecting them (e.g., through catheters) or tracking them to assure that they are not again depositing or collecting (as in intravenous or cerebrospinal fluid blockage), or moving in segments which are too large and could cause blockage in other parts of the body as they are carried about.

Unfortunately, with in vivo delivery of materials (particularly extremely small doses in small volumes delivered by small instrumentation into tissue regions protected by the blood-brain barrier, or the brain-cerebrospinal fluid barrier, or into visually inaccessible areas), it has not been possible to observe real time distribution of the material delivery, or the dispersion or distribution of the material at the injection or infusion site within the tissue. Where even small variations or miscalculations about the location of the target sight and the delivery device can significantly affect the delivery of material and the effectiveness of the delivered material, real time observation of the material delivery is even more critical than in topical or gross (e.g., massive systemic injection) delivery events. There has been no truly effective observation system for such delivery, including delivery made by or in conjunction with magnetic stereotaxis guidance of the drug delivery system prior to the present invention.

The invention comprises a device and method for targeted intracranial drug delivery using nonlinear magnetic stereotaxis combined with real-time magnetic resonance (MR) imaging or X-ray visualization guidance and, where appropriate, additional use of conventional methods of catheter manipulation. In one preferred embodiment, the MR-visible catheter drug delivery device is guided into the distal cerebrovasculature using a combination of flow-directed, manual manipulation, and magnetic stereotaxis steering without reducing cerebral perfusion in the affected vascular territory. Some general features of magnetic stereotaxis or magnetic surgical procedures are described in the text that follows. Specific procedures will depend on the nature of the patient's malady, the location and accessibility of the lesion or target location, and the mode of use selected by the clinical operator of the magnetic stereotaxis or magnetic surgery system. In a nonlinear magnetic stereotaxis procedure, the following procedures, with desired clinical variations, provide an example of practice of the present invention. The patient may be first fitted with fiducial markers that are fixed to the skull and which are visible in both MR and x-ray images. After these markers are placed in an appropriate array on the skull, the patient is given a pre-operative MR brain scan, the results of which constitute an atlas of images that define the location of critical brain structures and any potential target locations (e.g., a specific part of a tumor) relative to the fixed fiducial markers. The atlas of images is then stored in the host computer system used by the clinician to control the magnetic stereotaxis system. Near real time, real time, or on-the-fly MR images may also be obtained and might be used to control the magnetic stereotaxis system (although this would interrupt the magnetic stereotaxis procedure to some and perhaps a large degree), and in fact, real time images provide a potentially more accurate guide path. Following any additional pre-operative procedures that might be indicated for the patient's condition (eg., sedation, fall or partial anesthesia, etc.), the patient who will undergo an intraparenchymal magnetic surgery has a burr hole opened in their skull to allow the clinician an access port to insert the implant that will be magnetically guided to the intracranial target. Following placement of the implant on the pial surface of the brain within and at the bottom of the burr hole, the patient then rests their head within the configuration of coils that are used to apply magnetic forces and torques to the implant, and the clinician operates the bi-planar fluoroscopy system and other controls of the magnetic stereotaxis system. The resulting images provide 3-dimensional information about the location of the implant relative to the skull markers, and these data are superimposed and registered onto the pre-operative MR brain scan (near real time, real time or a more recent scan) so that the clinician can determine the initial position of the implant in relation to critical brain structures and/or target locations within the brain. The clinician then enters commands into the magnetic stereotaxis system's user interface that instruct the system how far to move the implant and in what specific direction. This can be done in one instance by using cursor-cross hairs, screen contact pencils, virtual drawing systems, or other graphic or viewable drafting systems on a computer screen to indicate the present location of the implant's tip and to select the next location to which it is to be moved. The clinician then instructs the system to execute this movement command and the system uses its control algorithm to produce magnetic fields that steer the magnetic tip of the implant appropriately while the body of the implant is pushed forward, as might be done by a motor-actuated guide-wire that traverses the interior of the implant/catheters/lumen, and abuts against the rear side of the tip of the implant. Biplanar fluoroscopic images are obtained during the movement sequence to localize the new position of the tip of the implant. In some variations of this procedure and with reference to prior art cited above, a multiple lumen catheter is used as the implant, and the magnetic tip of the catheter (fixed to one of the interior sub-catheters) can then be withdrawn from the implant once it is properly in place, and some other mechanism or therapy deliver device can be inserted through the outermost lumen of the catheter in place of it to perform the indicated diagnostic or therapeutic task. The implant can then either be withdrawn or left in place for any subsequent treatments that might be needed.

If the magnetic stereotaxis system is to be used as a method of delivering therapies into the cerebrovasculature, then in a maimer similar to the way that interventional neuroradiological procedures are now carried out, the implant/catheter would be introduced into the body perhaps through the femoral artery and guided into the brain. The process for intra-endovascular versus intraparenchymal manipulations is rather similar, in that a pre-operatively obtained atlas of appropriate images is used as a "road map" against which the navigation of the implant is carried out. A high resolution digital subtraction angiography atlas might be used in this case, to insure that the clinician is able to identify the vascular structures through which the implant must be moved. If the implant must be guided through vessels in which its path of movement is parallel to the flow of the blood, then the implant's movement can be partially flow-guided. Whether this is so or not, the tip of the implant is steered in the proper direction at vascular bifurcations by use of the magnetic fields to re-orient the tip as needed. The movement of the tip can be actuated by a pusher-wire or guide-wire inserted into the lumen of the implant/catheter and either driven by motor or advanced by hand, as appropriate to the implant's location, direction of movement, and targeted point of delivery. Ongoing biplanar fluoroscopy and post movement biplanar fluoroscopy are carried out for purposes of monitoring the implant's location, in ways analogous to the case of intraparenchymal magnetic manipulation described above.

Some additional general features of a magnetic stereotaxis or magnetic surgery procedure are the following. In the case of the use of a multi-coil superconducting "helmet" arrangement of the magnetic manipulation coils, the patient lies on a bed or gurney located in contact proximity with the front of the helmet, such that the patient's head can then comfortably rest inside the interior of the helmet's structure. The patient's head is immobilized on a headrest within the helmet's structure so that it does not inadvertently move during the procedure, thus introducing error and or time-delays into the imaging and image registration processes. Intraparenchymal magnetic movements would all take place in small increments and at very low rates of displacement, typically 1 mm/s or less. The intra-operative biplanar fluoroscopy is generally carried out so as to minimize the overall radiological dose received by the patient, consistent with the need for clarity in the images when that is called for. In the case of intravascular magnetic manipulation, the rate of displacement of the implant's tip through the vessel it is traversing will depend on the inside diameter of that vessel, the complexity and tortuosity of the vessel's structure and path, and the degree and direction of the blood flow in the vessel. The decision as to the selection of the rate of displacement is made by the clinician administering the treatment, using these and other factors to decide. In either case, the therapeutic agent to be delivered into the targeted area is pumped or otherwise transported through the lumen of the implant's catheter and allowed to exit from the tip of the implant or through selected regions of the side of the catheter (if it is made of a semi-permeable material). The therapeutic agent can thus be infusively pumped into the interstitial space of the brain (in the case of intraparenchymal infusion), perfused through endothelial walls of the arterial capillaries and into the brain, or retroperfused through the venous vasculature and into the brain. To flrther minimize the adverse effects of improperly located retroperfusion or delivery devices, the magnetic stereotaxis guided systems of the present invention can be magnetically guided during actual drug delivery to provide the maximum quality response to diagnosis of improper or inefficient delivery. Additional interoperative Magnetic Resonance Imaging would not perturb the location of the implant that was guided by Magnetic Stereotaxis, when the magnetic tip of the catheter implant is withdrawn prior to subsequent imaging and as long as the body of the catheter or implant is not made of permanently magnetic or magnetically permeable material. In general, a magnetic resonance imaging system would interfere with magnetic stereotaxis guidance (and vice versa) during mutual operation.

In either the intraparenchymal or intravascular applications, a magnetic stereotaxis procedure may alternatively be used to tow an intracranial electrical mapping or intracranial stimulation electrode or plurality of such electrodes, or some other solid object, such as a wire, filament, contact, lead or optical fiber or optical fiber bundle, into the brain or the cerebrovasculature for diagnostic or therapeutic purposes. The magnetic manipulation process would closely resemble that described above for the movement of an implant/catheter combination. MR Imaging would then be carried out to verify that the implant or object was properly positioned, providing, of course, that the imaging process would not jeopardize the safety of the patient by risking movement or heating of the implant or object.

The intracranial drug delivery device has at least one MR-visible marker, and preferably a linearly arranged array of radio-opaque and MR-visible markers disposed along its length to provide easily identifiable reference points for trackability and localization under susceptibility and active MR imaging, and under the bi-planar X-ray fluoroscopy used during nonlinear magnetic stereotactic guidance. Moreover, the tip of the intracranial drug delivery device would be fabricated such that it can be seen on MR and x-ray images and thus localized within the brain and/or spinal cord. The location of the tip of the drug delivery device is therefore known and the source point of the injection or infusion can thus be seen relative to the location of the device.

In a characteristic embodiment of the technique, an MR-compatible osmotic pump or some other flow-driving device is connected to a variable-length concentric MR-visible microdialysis probe with a variable molecular weight cut-off membrane or some other infusion device with a magnetic tip. This assembly is directed by nonlinear magnetic stereotaxis to the cerebrovascular, periventricular, intracerebroventricular, subarachnoid, intra parenchymal or intracerebrovascular site of the lesion. With the magnetic tip then either removed, safely positioned, or otherwise inactivated, the proper location of the probe is verified by M imaging and additional nonlinear magnetic stereotactic maneuvering, if necessary, is carried out. The pump circulates a diagnostic or therapeutic drug solution containing an MR-visible contrast agent through the walls of the dialysis fiber into the brain parenchyma or cerebral vasculature at rates between 0.01 nanoliters per hour to 10 milliliters per minute. The delivery and distribution kinetics of cerebrovascular, cerebrospinal fluid, and parenchymal injections or infusions of drug agents are monitored quantitatively and non-invasively using real-time contrast-enhanced magnetic susceptibility MR imaging combined with water proton directional diffusion MR imaging, and the response of the patient (in the case of therapy delivery) is tracked during this treatment. The distribution, pharmaco-kinetics, and (in some cases) clearance processes for the retroperfused or otherwise infused agent are tracked using the "Method and Apparatus for Use with MR Imaging" taught by Kucharczyk and Moseley (U.S. patent application Ser. No. 08/857,043, filed on May 15, 1997 and titled "Method and Apparatus for Use with MR Imaging").

The basic operation of the present invention therefore involves the initial MR imaging observation of a molecular environment of a patient or a target (e.g., a particular area or region of a patient, such as tissue, particularly such tissue as that present in organs or systems of animal bodies and especially the human body, including, but not limited to the intracranial compartment and the various anatomic regions of the brain, including the cerebral ventricles, cisterns, epidural and subdural spaces, sinuses, and blood vessels, the spinal cord, and spine, including disks, nerves and associated vascular system, the heart and the coronary vascular circulation, liver and the hepatic vascular circulation, kidney and the renal vascular circulation, spleen and the splenic vascular system, gastrointestinal system, special senses, including the visual system, auditory system, and olfactory system, the lymphatic system, the endocrine system including the pituitary gland, thyroid gland, adrenal gland, testes, and ovaries, and the peripheral parts and limbs of the body, with observation of an MR image signal intensity at a given time and/or state (e.g., prior to material introduction or at some defined stage of material diffusion into the molecular environment. In an example of the method of the invention, the drug delivery device is positioned by magnetic stereotaxis and viewed when possible and appropriate in real time by MR imaging or X-ray fluoroscopy to confirm that the device is properly positioned in a desired region (if not precise location) within a patient's body. Then the distribution of the delivered material in the tissue is determined (viewed by MR real time imaging) by releasing an amount of the material through the drug delivery device (which was already positioned in the tissue by magnetic stereotaxis and location-confirmed) while being observed with Magnetic Resonance Imaging, allowing the material to diffuse or perfuse into the tissue, and analyzing the resulting MR signal intensity. On a continual basis or at some subsequent time interval later (so as to conserve energy requirements or minimize the treatment time to or other possible effects on the patient, e.g., by a pulsed interval, preselected interval, random interval, frequent or sporadic intervals), the MR image of the molecular state within the same general area is observed. Changes in the characteristics, properties or quality of the image, such as the image signal intensity within the area are presumptively (and in most cases defnitively) the result of the introduction of material into the original molecular environment and alteration of the MR response for regions of the environment where delivered material concentration has changed. By repeating observation of the MR image signal intensity within an area at least once (e.g., first taking the initial observation at a material concentration state at a time $T_1$, and at least one subsequent observation of MRI-observable changes such as in the signal intensity qualities at a time $T_2$), the change in MR image signal intensity qualities can be related to the change in material concentration (in a region or at specific site locations or even within particular cell structures) between times $T_1$, and $T_2$, whether that change is from a starting point of zero concentration or from an existing concentration level. The observations therefore relate to the actual delivery of material into the molecular environment in an observable, and to some lesser degree, quantifiable manner.

The change in the signal, e.g., the change in the amplitude of the MR signal in the visible image may be altered by:

a) a change in the apparent diffusion coefficient (ADC) of tissue water protons;

b) a change in tissue magnetic susceptibility (BO);

c) a change in T1 tissue relaxivity (T1);

d) a change in T2 tissue relativity (T2);

e) a change in tissue magnetization transfer coefficients (MTC);

f) a change in tissue chemical shift frequency;

g) a change in tissue temperature; or h) a combination of any one or more of a)—g) alone or with other effects.

The MR signal is dephased by the random motion of diffiusing water molecules, and the presence of the delivered material locally affects the degree to which the amplitude of the signal is altered by the dephasing. If the amount of active ingredient to be delivered is quite small, or the effect of that material on the alteration of the amplitude is minimal, the delivered material may be associated with a larger amount of a second material or another more MR-signal-responsive material, which are preferably selected on a basis of similarity in diffusion rates through like materials or at least have comparable (mathematically relatable) diffusion rates. In this manner, using such a taggant material, the diffusion of the delivered material may be assumed to relate to the diffusion/delivery of the taggant material. Unlike other observational techniques, these taggant materials may be readily provided as non-toxic, inexpensive taggant materials since there is such a wide variety of materials which could be so used, and their only functional requirements would be diff-usion rate and non-toxicity. Many dyes commonly used in medical procedures could be used for this purpose.

The availability of an MR-visible drug delivery device, which can be guided and placed by magnetic stereotaxis and combined with a visible chemical or drug agent would make it possible to obtain near real-time information on drug delivery during interventional procedures in an intra-operative MR system, with pre- and post-imaging remote guidance of the delivery system via magnetic stereotaxis, or alternatively, real-time intra-operative guidance via an MR-based interventional technique, as well as for pre-operative and post-operative confirmation of the location of the drug delivery device. Medical and surgical applications would include vascular surgery and interventional radiology, cardiac surgery and cardiology, thoracic surgery and radiology, gastrointestinal surgery and radiology, obstetrics, gynecology, urology, orthopedics, neurosurgery and neurointerventional radiology, head and neck surgery and radiology, ENT surgery and radiology, and oncology. In addition to direct tissue injection, the method of the invention applies to drug delivery via intraluminal, intracavitary, laparoscopic, endoscopic, intravenous, and intra-arterial applications.

There is currently considerable interest in the therapeutic use of small ions as well as macromolecules in the treatment of various neurologic diseases. To be effective, such molecules must be able to reach target tissue receptors. Many molecules that are used in therapeutic drugs are large in size, for example, neuroleukin, a neuromodulator drug tested for treatment of amyotrophic lateral sclerosis is about 56 kDa, bethanechol chloride used in treatment of Alzheimer's Disease is about 196 kDa and nerve growth factor is about 13 kDa While the importance of large molecular weight molecules in direct parenchymal drug therapy is growing, little is known about the time course and the spatial range of their actions, since dynamic visualization methods for studying the spread of macromolecular species within the brain are not typically available.

Partly because of this, several significant efforts recently have been undertaken towards the goal of developing an understanding of the diffusion of various molecular species through the interstices of the neural tissues. The work has followed two general lines of activity: (1) the development of new experimental approaches that overcome the existing limits on the laboratory study of the temporal and spatial distribution patterns produced by the diffusion or spread of an agent through the central nervous system (CNS), and (2) attempts to analytically describe this process in terms of suitable mathematically-based biophysical models of the diffusion or spread of such agents through the CNS. In addition to understanding the diffusion-based transport of metabolic or therapeutic agents in the brain, it is also important to have a clear perception of the intusion-based transport of such agents. This is because such agents would typically be delivered in aqueous solution (or at least in liquid form) by a drug-delivery catheter that inserts them, e.g., into the parenchymal tissues under conditions in which pressure gradients can and typically would subsequently exist in the brain (at least within regions of the brain in the vicinity of the infusion site). These gradients, in turn, can and typically do produce hydrodynamic driving forces on the infused solutions. Both biophysical mechanisms, infusion and diffusion, contribute to the movement of molecules through the CNS and both are important delivery processes that could be enabled and would be optimized by the subject invention, i.e., an MR visible catheter that can be placed within the brain or neurovasculature via magnetic stereotaxis. Those features of these mechanisms that are important within the context of the subject invention and which help to reveal its full utility are presented below.

Basser has developed a biophysical model for infusions through a porous medium like the brain ("Interstitial Pressure, Volume, and Flow during Infusion into Brain Tissue," Microvascular Research, Vol. 44, pps. 143–165, 1992). In particular, he uses a consolidation model to predict the dynamic response of the brain's structure to the pressure-driven infusion of a fluid within the brain. He then examines the pressure and flow distributions for infuisates pumped into the brain under four different conditions. (1) infusion from a constant pressure source, (2) infusion from a constant flow source, (3) step infusion from a pressure source, and (4) step infusion from a constant flow source. infusion from a constant pressure source is a model that is applicable to the delivery of drugs into the bulk brain tissues, and one of the results of Basser's study is the prediction that the velocity, $V_r(r)$, of the fluid infused within the brain is a function of the radial distance, r, from the infusion point, and that the specific prediction is that $V_r(r)=kP_o a/r^2 f$ where k is the hydraulic conductivity of the brain matrix material, Po is the pressure within the cavity created in the brain matrix at the tip of the infusion source (eg., the catheter tip) by the initial influx of fluid, a is the radius of the initial infusion cavity, and f is the volume fraction of the interstitial space relative to the total brain volume. The penetrability of fluids agents delivered via pressure-driven infusion is generally different from that associated strictly with diffusion of the same substances, since the driving mechanisms are different (infusion: flow along a pressure gradient; diffusion: flow along a concentration gradient). This is an important point since diffusion alone may not constitute a completely effective driving mechanism for all of the different fluid agents that must penetrate certain regions of the brain e.g., those with elevated interstitial pressure, such as solid tumors (for a discussion of elevated intersitial pressure in tumors, see Netti et al., "Time-Dependent Behavior of Interstitial Fluid Pressure in Solid Tumors: Implications for Drug Delivery," Cancer Research, Vol. 55, pps. 5451–5458, 1995). Moreover, Morrison et al. ("High-Flow Microinfusion: Tissue Penetration and Pharmacodynamics," American Journal of Physiology, Vol. 266, ps. R292-R305, 1994) have shown that volumetric infusion rates of 0.5 µl/min and above are potentially able to provide dosages of agents to much larger volumes of brain tissues than are possible with lower-flow rate methods. These points, taken in conjunction with clinical testing of the infusion concept (Lieberman et al., "Convection-Enhanced Distribution of Large Molecules in Gray Matter During Interstitial Drug Infusion, Journal of Neurosurgery, Vol. 82, pps. 1021–1029, 1995; Laske et al., "Chronic Interstitial Infusion of Protein to Primate Brain: Determination of Drug Distribution and Clearance with Single-Photon Emission Computerized Tomography Inaging, Journal of Neurosurgery, Vol.87, pps. 586–594, 1997; Broaddus et al., "distribution and Stability of Antisense Phosphorothioate Oligonucleotides in Rodent Brain Following Direct Intra parenchymal Controlled-Rate bIfusion," Neurosurgical Focus, Vol. 3, No. 5, Article 4, 1997), suggests the utility of the method for treating a wide variety for neurological disorders, providing that a suitable means of placing the catheter within the brain and verifying its proper location therein can be employed. The present invention provides appropriate methodology for allowing this to happen.

Diffusion of drug and/or water protons in a complex medium, such as a brain cell microenvironment, is influenced by numerous factors. Materials injected into the brain or spinal cord do not move unimpeded through the aggregations of neurons, glia, capillaries, and nerve fibers. The distribution of a drug volume in the brain cell microenvironment following injection directly into brain tissue is governed by a number of factors including the physicochemical characteristics of the drug, capillary uptake, metabolism, excretion, size of the extracellular space (the volume fraction), and geometry and topology of the brain cell microenvironment (tortuosity). The degree to which each of these factors influences the distribution of a particular drug agent within the brain or spinal cord is an important determinant of the effectiveness of drug treatment of diseases of the central nervous system.

Despite the fact that the average spacing between brain cells may be no more than 20 nm, the mean free path of an ion at the typical ionic strength of the mammalian nervous system (about 0.15) is only about 0.01 nm. In ways similar to altering the local ADC of the water protons, presence and transport of a drug through a tissue will also alter the magnetic susceptibility, T1, T2, MTC, water proton diffusion anisotropy, chemical shift frequency, and temperature of the protons within each imaged voxel. This represents the distance traveled between collisions with other molecules. Almost all these collisions actually take place with water molecules since the concentration of water is 55 M. Thus ions intrinsic to the brain rarely encounter cell membranes and generally behave as though they were in a free medium. However, the diffusivity properties becomes much more complicated when the boundary has a complex geometry, or when macromolecular interactions involve exogenous solutions injected into tissues.

In complex media such as brain tissue, diffusion obeys Ficks Law, subject to two important modifications. First, the diffusion coefficient, D, is reduced by the square of the tortuosity factor to an apparent diffusion coefficient $ADC^* = D/(\text{tortuosity factor})^2$ because a diffusing material encounters membranous obstructions as it executes random movements between cells. Second, the source strength is divided by the volume fraction of the extracellular space so that a given quantity of released material becomes more concentrated than it would have been in a free medium.

In most media, tortuosity and volume fraction are essentially dimensionless factors which depend only on the geometrical constraints imposed by local structures. In brain tissue, however, a third factor, non-specific uptake, is present in the diff-usion equation as a term, k', for loss of material across the cell membranes. In fact k' can be expressed as P (S)/volume fraction, where P is the membrane permeability and (S) is the volume average of the membrane surface area. Complex local boundary conditions imposed by cell membranes can thus be removed by averaging the local diffusion equations and boundary conditions over some characteristic volume of tissue a few micrometers in extent. Thus in the case where a substance is injected from a point source at a rate of q moles/s in a free medium, the source term becomes qitortuosity in a complex medium while the diffusion coefficient is modified to be $D/(\text{volume fraction})^2$ in the new equation, which then becomes a quantity related to the apparent diffusion coefficient, ADC.

Knowledge of the properties of the brain extracellular microenvironment is thus essential to understanding the role of diffusion in delivering metabolic or therapeutic agents to brain or spinal cord cells. Diffusion has been determined employing radioactive or fluorescent tracers, in which the concentration profiles of the tracer are monitored over time, and its diffusivity is inferred from the data. Microscopic displacements can be seen with tracers on the scale of millimeters. Spatially resolved methods, such as infrared spectroscopy or Rayleigh scattering, have been used allowing resolution in the micrometer range. Such tracer techniques have been successfully applied in biological systems, such as the brain. However, because of the inherent invasiveness of using exogenous tracers, such techniques cannot be used in vivo with humans.

Techniques have also been developed for determining the diffusion characteristics of small molecules in local regions of the brain using radiotracers, microiontophoresis, or pressure microinjection combined with ion-selective microelectrodes. The applications of these methods to intracranial drug delivery have been described in the medical literature, for example, Lux et al., Exp. Brain Res., 17, 1973, pp. 190–205, Gardner, Medwin, Neurosci. Res. Progr. Bull., 1980, 18, pp. 208–226, Nicholson et al., J. Physiol., 1981, 321, pp. 225–257, Nicholson et al., Brain Res., 1979, 169, pp. 580–584. However, these techniques have several key limitations. First, these techniques provide a measurement at only a single point in the tissue so that spatial patterns of diffusion cannot be determined. Second, ion-selective microelectrodes can only be used with a few small ions. Third, radiotracer techniques rely on postmortem counting of particles in fixed and sectioned tissues, and they provide limited spatial resolution with no dynamic information.

Several previous studies have obtained estimates of the ADC of large fluorescent molecules from digitized images of fluorescent molecules as they diffused away from blood vessels. However, the complicated geometry of the source and inability to precisely characterize the emitted flux, substantially limit the clinical utility of the information. Similarly, new optical imaging methods, in which a uniform distribution of fluorescent tracer is first established in the sample and then a region is photobleached with a strong laser, has serious limitations because the laser beam can also damage the tissue area being imaged. Studies with optical fluorescence methods suggest that molecules as large as 70 kDa can pass through the brain extracellular microenvironment. Further studies with positive pressure infusion, however, show that Blue Dextrain molecules with molecular weights of 2,000,000 can be pumped through the interstitial space of the brain. (S. S Prabhu, W. C. Broaddus, G. T. Gillies, W. G. Loudon, Z. J. Chen, and B. Smith, "Distribution of Macromolecular Dyes in Brain Using Positive Pressure Infusion: A Model for Direct Controlled Delivery of Therapeutic Agents," *Surgical Neurology*, Vol.49 (1998).

Below some limit between 10 and 40 kDa, molecular diffusion is not restricted any more than with much smaller molecules. Similar constraints have been found for diffusion in the brain intracellular microenviromnent, whereby all molecules diffuse at least three times slower than in aqueous solution, suggesting a similar tortuosity in the intracellular environment.

An integrative optical imaging technique disclosed by Tao and Nicholson, Biophysical J., 1993; 65, pp. 2277–2290 yields an apparent diffusion coefficient from digitized images, and enables precise determination of the diffusion characteristics of fluorescently labeled compounds of high molecular weight. The generalized equations disclosed by Nicholson and Tao have two nondimensional factors that incorporate the structure of the tissue into the imaging solution. The first factor, the tortuosity, accounts for the hindrance to extracellular diffusion that arises from the obstructions presented by cell membranes. The second structural factor is the volume fraction, which is defined as the ratio of the volume of the brain extracellular microenvironment to the total volume of tissue averaged over some small reference domain. The method disclosed by Nicholson and Tao ("Hindered diffusion of high molecular weight compounds in brain extracellular microenvironment measured with integrative optical imaging." Biophysical J. 1993; 65:2277–2290) does not, however, yield a direct measurement of the molecular distribution in a three-dimensional sample, and furthermore requires the use of large fluorescent markers which are not suitable for repeated injections in human patients.

An alternative approach to measuring difflusivity of therapeutic drug injections is to monitor the diffusion process itself, i.e., the random motions of an ensemble of particles. Einstein showed that the diffusion coefficient measured in nonequilibrium concentration cell experiments is the same quantity that appears in the variance of the conditional probability distribution, $P(r/r_o, t)$, the probability of finding a molecule at a position r at a time t, which was initially at a position $r_o$. For free diffusion, this conditional probability distribution obeys the same diffusion relation. Thus, MR imaging parameters which reflect the differences in relative water proton-diffusion path lengths may serve to enable imaging differentiation between tissue water protons and protons in macromolecular solutions that are injected into brain tissues.

Molecular water-proton diffusion is caused by thermally induced random Brownian motion. As the protons continually collide with their microenvironments, their average random traveled pathlength <L>, along one direction (e.g., along the magnet-bore direction) is described according to Einstein as: $<L^2>=2\ TD$ where over an observation time of T (seconds) the displacement is expressed by a "diffusion coefficient, D" in $r=2/S$ or $CM^2/S$. The diffusion process is continuous, so that the average displacement of any population of water protons increases with MR imaging time. However, the diffusion behavior of protons can be hindered by impermeable or semi-permeable barriers, such as cell membranes, and macromolecules, which may themselves contain populations of diffusing protons. For tissue water protons diffusing within a tissue matrix, the observed diffusion rate and direction will reflect the molecular and macromolecular barriers or hindrances that the diffusing protons encounter during their translational processes. One example of the application of this concept in human neurobiology is that myelinated nerve fibers in the brain and spinal cord preferentially dispose the diffusion of water protons along, rather than across, myclin tracts thereby giving rise to diffusional anisotropy MR imaging properties (oseley et al., Mag. Res. Med., 19,1991, pp. 321–326, Moseley et al., Topics Mag. Res. Med., 3, 1991, pp. 5068).

Although noted for its effects on high-resolution, high-field MR spectra more than 25 years ago, molecular (water proton) diffusion has just recently been shown to have an important impact in clinical MR neuroimaging applications. While T1 and T2 relaxation times reflect frequency-dependent rotational and proton exchange processes, diffusion is caused solely by molecular or proton displacements or translations. Molecular size, shape, microenvironment, and temperature all influence the diffusion rate of molecules.

Generally, larger molecules will translate (diffuse) more slowly than smaller molecules, such as water protons, and the differences in diffusion rates between different populations of molecules can be distinguished by signal intensity differences on diffusion-weighted MR images, particularly MR images which employ large diffusion gradients (b values). Thus, the measurable diffusion of smaller versus large molecules with MR imaging can be used as an in vivo tracer to probe the structural orientation of the tissues into which the drug agent has been injected. Advances in diffision-weighted MR imaging have been made possible by major technical improvements in MR scanner hardware and software. High-speed MR echo-planar imaging now enables subsecond diffusion-sensitive imaging of water proton behavior in brain and spinal cord.

Thus, MR-visible molecules may exist in a variety of environments in brain tissue, which modify the way in which the molecules can move. First, the space in which the molecules can move may be small (e.g., intracellular) or large (e.g., an enlarged extracellular space). Second, the amount of dissolved compounds and proteins may alter the viscosity of the substance injected into the tissue. The random movement of the molecules is characterized by its diffusion coefficient ADC as the mean square distance moved for unrestricted isotropic (i.e. same in all directions) diffusion (for example a large sample of pure water). ADC is high in pure water, and lower by about a factor of 10 in tissue. As tissue becomes destroyed by disease processes, ADC is expected to rise toward its free water value. A prerequisite for MRI-guided drug delivery into the brain parenchyma or cerebral vasculature is the availability of suitable access devices. Representative of dilatation catheters having a coating which releases a therapeutic agent is U.S. Pat. No. 5,102,402 to Dror, in which a microencapsulated compound is released upon expansion of the dilatation balloon into contact with the surrounding tissue. U.S. Pat. No. 5,171,217 to March describes the delivery of several specific compounds through direct injection of microcapsules or microparticles using multiple-lumen catheters, such as disclosed by Wolinsky in U.S. Pat. No. 4,824,436. U.S. Pat. No. 5,120,322 to Davis et al. describes the process of coating the surface layer of a stent or shunt with lathyrogenic agent to inhibit scar formation during reparative tissue formation, thereby extending exposure to the drug agent. U.S. Pat. No. 5,057,106 to Kasevich discloses the use of microwave energy for heating atherosclerotic plaque in the arterial wall in combination with dilatation angioplasty. U.S. Pat. No. 4,807,620 to Strul and 5,087,256 to Taylor are examples of catheter-based devices which convert electromagnetic radiofrequency (RF) energy to thermal energy. U.S. Pat. No. 5,628,730 to Shapland et al discloses a phoretic balloon catheter with hydrogel coating which can be used to deliver drugs locally to internal body tissues under x-ray visualization. U.S. Pat. No. 5,720,720 to Laske et al. Describes a catheter-based high-flow microinfusion method which has been used to infuse substances up to 1 cm from the delivery source.

The patented inventions referenced above provide useful methods for introducing, delivering, or applying a drug agent to a specific target tissue, but each invention also has inherent limitations, some of which can lead to technical and clinical difficulties. With currently used catheterization techniques, there is generally a compromise between longitudinal and torsional rigidity for advancing and negotiating progressively more tortuous and narrow vascular lumens. As a result of these limitations associated with transarterial and transvenous manual catheterization, there has been growing interest in using magnetic fields to guide catheters through the cerebral vasculature. As an example of another common catheter design problem, catheter systems which provide endovascular drug delivery either require temporary blocking of a segment of the vessel, or the use of significant transluminal pressures to induce penetration of the drug agent into the vessel wall or plaque layer. Microencapsulated coatings on catheters permit longer exposure of the tissue to the drug agent, but the physical limitations imposed by microcapsules restrict the volume and concentration of drug that can be effectively applied to any tissue area. Exposed coatings on catheters which contain drug agents usually require some type of sheath that must be removed from the catheter before the drug can be released from the coating. The sheath and any catheter components required to physically manipulate the sheath greatly increase the profile of the catheter, and may thereby limit the variety of applications for which the drug delivery system can be employed. Furthermore, the binders or adhesives used in catheter coatings may themselves significantly dilute the concentration of the therapeutic agent. Finally, thermal and luminous energy required to melt and bond coatings such as macroaggregated albumin, to reduce tissue mass by ablation, and to inhibit restenosis by cytotoxic irradiation may also cause damage to blood vessels.

U.S. Pat. No. 5,470,307 to Lindall discloses a low-profile catheter system with an exposed coating containing a therapeutic drug agent, which can be selectively released at a remote tissue site by activation of a photosensitive chemical linker. In the invention disclosed by Lindall, the linker is attached to the substrate via a complementary chemical group, which is functionalized to accept a complementary bond to the therapeutic drug agent. The drug agent is in turn bonded to a molecular lattice to accommodate a high molecular concentration per unit area and the inclusion of ancillary compounds such as markers or secondary emitters. Although U.S. Pat. No. 5,470,307 to Lindall describes significant improvements over previous catheter-based drug delivery systems, the disclosed invention nonetheless has numerous problems. First, in common with other currently used endovascular access devices, such as catheters, microcatheters, and guidewires, the catheter tip is difficult to see on MRI because of inadequate contrast with respect to surrounding tissues and structures. This makes accurate localization difficult and degrades the quality of the diagnostic information obtained from the image. Thus, one objective of the present invention is to provide for an MR-compatible and visible vascular access device that significantly improves the efficacy and safety of cerebroendovascular drug delivery using MR guidance and/or nonlinear magnetic stereotaxis, e.g., for retroperfIsion therapies.

Any material that might be added to the structure of a pliable catheter in order to make it MR visible must not make the catheter magnetically susceptible, or imaging artifacts could be introduced during the MR process. Moreover, forces might be applied to such a catheter by the magnetic manipulation coils of the nonlinear magnetic stereotaxis system. In either case, the safety and efficacy of the procedure might be jeopardized, with resulting increased risk to the patient. Also, an MR-visible catheter must be made of material that is temporally stable, of low thrombolytic potential, and which is unlikely to damage any scar tissue formations if it is to be left indwelling in either the parenchymal tissues or the cerebral vasculature.

Guidewires are usually made of radio-opaque material so that their precise location can be identified during a surgical procedure through fluoroscopic viewing. Exemplary of guidewires used under X-ray viewing is the guidewire disclosed by LeVeen, U.S. Pat. No. 4,448,195, in which a radio-opaque wire can be identified on fluoroscopic images by metered bands placed at predetermined locations. The U.S. Pat. No. 4,922,924, awarded to Gambale et al. discloses a bifilar arrangement whereby radio-opaque and radiotransparent filaments are wrapped on a mandril to form a bifilar coil which provides radio-opaque and radiotransparent areas on the guide wire. U.S. Pat. No. 5,569,197 to Helmus and Forman discloses a drug delivery guidewire formed of super elastic materials which can be used as a drug delivery device in thrombolytic and other endovascular procedures. However, all of these guidewire materials are difficult to see on MR images because they fail to produce sufficient contrast with respect to the surrounding body tissues. This lack of MR visibility is also a problem for most commercially available catheters, microcatheters and shunts.

Attempts to visualize endovascular devices in MR imaging have generally been based on the passive susceptibility artifacts produced by the device when exposed to the MR field. Image distortion may include general signal loss, regional signal loss, general signal enhancement, regional signal enhancement, and increased background noise. U.S. Pat. No. 4,572,198 to Codrington provided for conductive elements, such as electrode wires, for systematically changing the magnetic field in a defined portion of the catheter to yield increased MR visibility of that region of the catheter. However, the presence of conductive elements in the catheter also introduces increased electronic noise and the possibility of Ohmic heating, and these factors have the overall effect of degrading the quality of the MR image and raising concerns about patient safety.

U.S. Pat. No. 5,154,179 and 4,989,608 to Ratner disclose the incorporation of paramagnetic material into endovascular devices in order to make the devices visible under MR imaging. However, these patents do not provide for artifact-free MR visibility in the presence of rapidly alternating magnetic fields, such as would be produced during echo-planar MR imaging pulse sequences used in real-time MR guidance of endovascular procedures. Nor do these patents teach a method for monitoring with MR visible catheters the outcomes of cerebroendovascular therapeutic interventions; for example, embolotherapy of cerebral aneurysms or arteriovenous malformations. Ultrafast imaging sequences generally have significantly lower spatial resolution than conventional spin-echo sequences. The magnetic susceptibility artifact produced by the device must be small enough not to obscure surrounding anatomy, or mask low-threshold physiological events that have an MR signature, and thereby compromise the physician's ability to perform the intervention.

A second problem with currently available endovascular devices relates to whether they can be used safely with high speed MR imaging procedures. The force on a ferromagnetic or permanent magnetic object in a magnetic field is, to a good approximation, given by the product of the object's magnetic dipole moment and the gradient of the magnetic field. Thus, it is important that endovascular devices used under MR guidance are MR-compatible in both static and time-varying magnetic fields. Similar considerations call for such devices to be compatible with the fields produced by the magnetic stereotaxis system, too. Although the mechanical effects of the magnetic field on ferromagnetic devices present the greatest danger to patients through possible unintended movement of the devices, tissue and device heating may also result from radio-frequency power deposition in electrically conductive material located within the imaging volume. Consequently, all cables, wires, and devices positioned within the MR imager or the magnetic stereotaxis system must be made of materials that have properties that make them compatible with their use in human tissues during MR imaging procedures or magnetic stereotaxis procedures.

U.S. Pat. No. 5,647,361 to Damadian discloses a catheter with guidewire whose position can be precisely controlled by piezoelectric actuators. However, unlike the present invention, the invention disclosed by Damadian does not provide for in vivo magnetic manipulation and selective navigation of blood vessels and bulk-tissue movement in the brain.

In the method of the invention, a retroperfusion catheter or other drug delivery device is placed by nonlinear magnetic stereotaxis, and is subsequently visualized and localized by its susceptibility artifacts on both conventional spinecho and ultra-fast imaging sequences. Alternatively, in another method of the invention, the drug delivery device is visualized by the presence of one or more MR visible microcoils placed along the distal axis of the microcatheter. Imaging for visualization purposes is done after positioning of the microcatheter by nonlinear magnetic stereotaxis. MR visibility is variably adjustable based on requirements related to degree of signal loss for device localization and positioning, enhancement along the shaft of the device, enhancement around the body of the device, visibility of the proximal and distal ends of the device, degree of increased background noise associated with the device movement, and other factors which either increase or suppress background noise associated with the device.

The method of the invention can be used within a wide range of medical procedures as in, for example, a) providing for a temporary life-support system in stroke patients based on microcatheter retroperfusion of acutely ischemic brain tissue using nonlinear magnetic stereotaxis and MR imaging and/or X-ray guidance; b) for catheter-based administration of thrombolytic agents, MR-visible contrast media, or cerebroprotective anti-ischemia drugs, such as sodium and calcium neuronal membrane channel blockers, NMDA antagonists, glycine partial agonists, adenosine agonists and antagonists, calpain inhibitors, endothelin antagonists, anti-adhesion antibodies, antiphospholipid antagonists, and nitric oxide derivatives linked to blood-brain banier transport vectors, such as liposomes, or perhaps to blood-brain banier permeabilizing agents; c) for pre- and post-surgical endovascular treatment of tumors of the brain by acute, subacute and chronic infusion of therapeutic drug agents, neurotoxins, anti-angiogenesis factors, devascularization embolotherapy agents, anti-emetics, and anti-nausea agents linked to blood-brain barrier transport vectors, such as liposomes or blood-brain barrier permeabilizers; d) the catheter device can be used as a modified stent device to preserve the patency of intracranial venous blood vessels and sinuses which are either blocked by plaques or mechanically compressed by brain tumors, trauma, infection, or edematous masses; e) the MR-visible drug delivery device can also be used to treat non-ischemic cerebral lesions, such as the plaques associated with multiple sclerosis and Alzheimer's disease, by targeted endovascular or intraparenchymal injection or infusion of neuropeptides, monoclonal antibodies and other gene-targeted therapies, growth factors, and other therapeutic agents, which may be linked to various bloodbrain transport vectors, such as liposomes or blood-brain barrier permeabilizers.

In one practice of the method of the invention, a multiple-lumen MR-visible microcatheter is directed into the venous neurovasculature or cerebral sinuses under nonlinear magnetic stereotaxis and its location is verified by MR or X-ray imaging. The walls of the outer catheter are made of MR-compatible materials such as, but not limited to elastomeric hydrogel, polymers (thermoset or thermoplastic), composites, fabric, reinforced film, or similar material, which have an intrinsic elastic memory which can be activated by increased temperature, surface wetting, or decreased pH. The outer catheter has an adjustable stiffness which provides uniform circumferential contact with the vessel endoluminal surface, and thereby enables dynamic compliance matching with the intracranial or extracranial vessel undergoing therapy. In one preferred embodiment, the exit port on the microcatheter tip can also expanded up to two gauge sizes when hydrated or otherwise activated to improve the efficacy of endovascular retroperfision of injured neuronal tissues.

In the general practice of the method of the invention, the MR-visible device, for example, a retroperfusion microcatheter, can be positioned in the venous intracranial circulation or dural sinuses under nonlinear magnetic stereotaxis and/or MR-imaging guidance. Cerebral delivery of drug agents or other biological materials is then monitored using contrast-enhanced magnetic susceptibility MR imaging or by active visualization via RF-Microcoils placed near the distal tip of the catheter. In cases of microcatheter migration, misplacement, disengagement, or compliance mismatch, the microcatheter can be retrieved and then subsequently repositioned by magnetic manipulation with minimal tissue damages. The MRvisible drug solutions may contain sterically stabilized liposomes, with lipophilic or hydrophilic chelators, such as DTPA on phosphatidyl ethanolamine or steric acid embedded within the external bilayer, or double-label liposomes that chelate a T2-sensitive metal ion within the internal aqueous space and another T1-sensitive metal ion on the outside surface, or liposomes which contain 100–1000 nm diameter bubbles of, for instance, argon, carbon dioxide, or air, as a contrast agent. Real-time contrast-enhanced magnetic-susceptibility-based MR imaging may be used to visually monitor the progress of neurovascular therapy. Changes in cerebral tissue perfusion are evaluated by bolus intravenous and intra-arterial injections of magnetic susceptibility contrast media, such as DyDTPA-BMA and GdDTPA-BMA, in combination with dynamic echo-planar MR imaging methods. Changes in cerebral perfusion are also evaluated by timed infusion of MR-visible sterically stabilized liposomes, with lipophilic or hydrophilic chelators, including the conjugation of DTPA on phosphatidyl ethanolamine or steric acid, embedded within the external bilayer. Cerebral perfusion is also evaluated with MR imaging following intravascular infusion of double-label liposomes that chelate a T2-sensitive metal ion within the internal aqueous space, and a T1-sensitive metal ion on the outside membrane surface. In another general embodiment the neurovascular device provides a temporary life support system in acute stroke patients by providing a device for retroperfusion of acutely ischeniic brain under MR Wnaging guidance, which can also monitor venous pressures and provide for pulsed-air inflation of an MR-visible angioplasty balloon at the distal end of the catheter.

DESCRIPTION OF THE PREFERRED EMBODIMENTS

With reference to FIG. 1 of the drawings, in the method of the invention the MR-visible microcatheter 1 has a shaft 2 made by conventional single extrusion technology of fluorinated ethylene-propylene copolymer, polytetrafluoroethylene, polychlorotrifluoroethylene, or similar commercially available material. From this example, the catheter would taper at the distal end 3 to about 0.020 and hence will accept a 0.018 guide- or pusher-wire 4 for mechanical advancement into the cerebrovasculature during nonlinear magnetic stereotaxis procedures. There may be approximately 0.5 to 20 cm (preferably from 0.5 to 3 cm) distal segment 7 made of hydrophilic cross linked polyurethane polymer containing polyoxyethylene and polyoxyethylene blocks, or from an elastomeric hydrogel formed from a polyurethane diacrylate composition, or from a multiple phase polymeric composition having a non-hydrophilic phase and hydrophilic phase in various preparations. In the method of the invention, the distal catheter segment 7 of the device has a softening index which can be programmed to change by 5- to 100-fold, and a physical expandability index which can be programmed to change by 1- to 3-fold over 3 min to 5 hours. In addition, the material used in the distal catheter segment 7 is non-thrombogenic and biocompatible, and has surface characteristics which bind and release drugs in a variably programmed manner. The catheter 1 which might be used for retroperfiision has a magnetic tip which allows it to be steered during nonlinear magnetic stereotaxis procedures. Both the catheter 1 and guide- or pusher-wire 4 have a linearly arranged array of radio-opaque and MR-visible markers 6 disposed at the distal end to provide easily identifiable reference points for trackability and localization under MR imaging and X-ray fluoroscopy. The microcatheter 1 can also be made from any of the well-known soft, biocompatible plastics used in catheter fabrication such as Percuflex, a trademarked plastic manufactured by Boston Scientific Corporation (Watertown, Massachusetts). When the catheter 1 is inserted into a patient, the distal markers 6 will be identifiable in an MR image and by X-rays, as will each of the other markers in the assembly. They can be formed of the well known radio-opaque materials such as gold, platinum or tantalum. An osmotic pump 7 and source of drug 8 is also shown.

Figure 2:
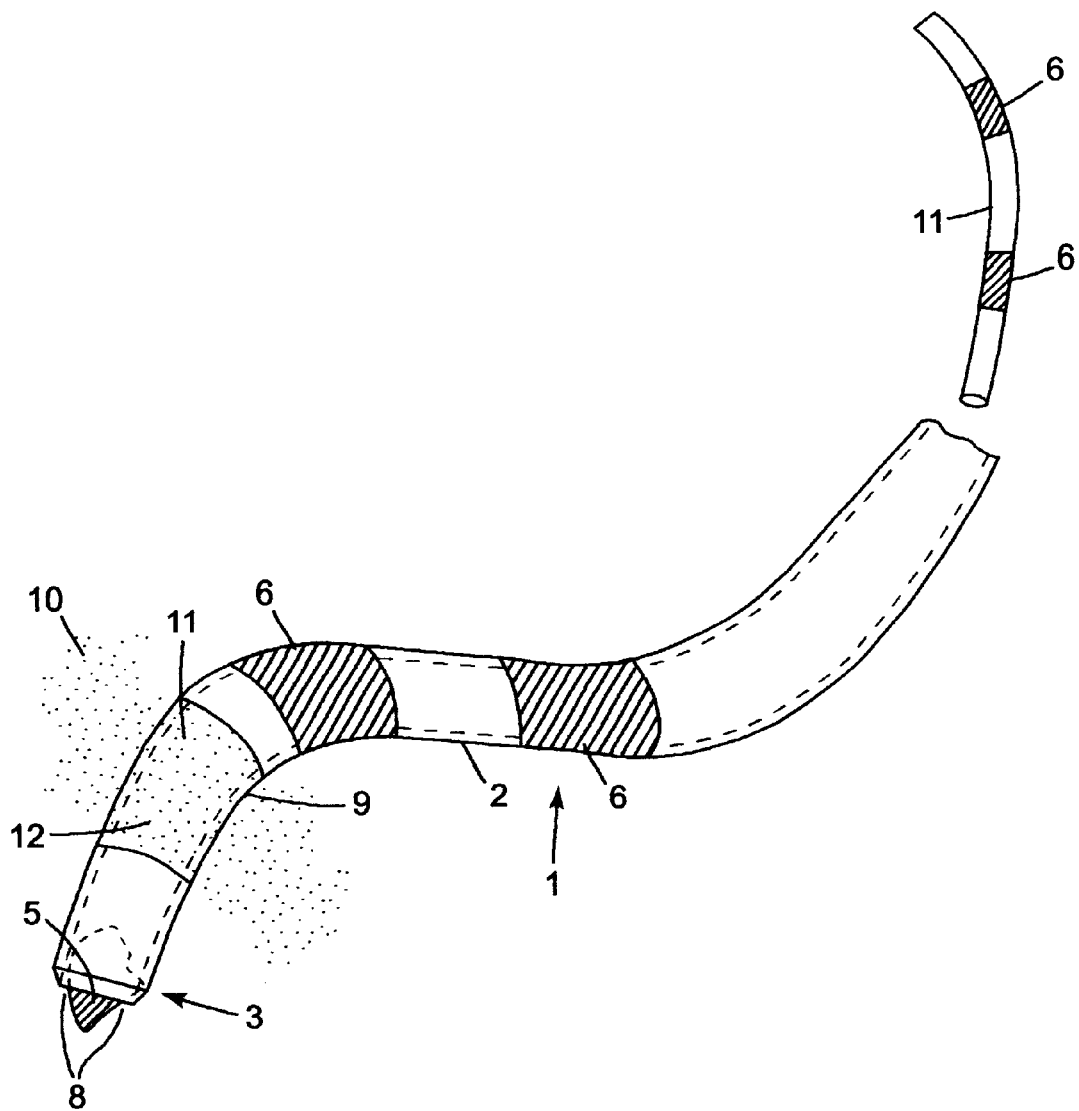
FIG. 2 is a view of another embodiment of the device according to the present invention, and it shows a flow diagram for practice of the process of the present invention wherein the drug delivery device is positioned by nonlinear stereotaxis under MR guidance and then delivery of a drug is monitored by visualization of delivery.

With reference to FIG. 2 of the drawings, the microcatheter device 1 is also employed to deliver pharmacologic therapies, in order to reduce morbidity and mortality associated with cerebral ischemia, intracrnnial vasospasm, subarachnoid hemorrhage, and brain tumors. In the method of the invention, an MR-compatible osmotic pump (not shown) is connected via flexible MR-compatible tubing 2 to a device 1 such as a variable-length, concentric, MR-visible microdialysis probe with a variable molecular weight cut-off membrane or other infusion device which is directed by nonlinear magnetic stereotaxis, MR guidance, or by more conventional methods, to the site of the lesion within the central nervous system. The device 1 comprises a magnetic tip 5 restrained by a hole 8 at the distal end of the device 1. A segment 9 allows the release of drug 10 (shown as dotted area) into a patient. Marker areas 6 are shown, as is a microcatheter with its own marker areas 6 which can be inserted into the device 1.

With reference to FIG. 2 of the drawings, in the method of the invention, surface modifications of the material components of the device 1 which will be considered a dialysis probe in this description, enables timed-release kinetics of MR-visible biologic response modifiers, including peptide macromolecules. The osmotic pump (not shown) circulates a therapeutic drug solution 11 containing an MR-visible contrast agent 12 through the walls of the dialysis fiber or other infusion device into the brain at rates between 0.01 nanoliters per hour to 10 microliters per minute. In the method of the invention, the MR-visible solution contains sterically stabilized liposomes, with lipophilic or hydrophilic chelators, such as DTPA on phosphatidyl ethanolamine or steric acid embedded within the external bilayer, or double-label liposomes that chelate a T2-sensitive metal ion within the internal aqueous space and another T1-sensitive metal ion on the outside membrane surface, or liposomes which contain 100–1000 nm diameter bubbles, for example of argon, carbon dioxide, or air, as a contrast agent.

Figure 3:
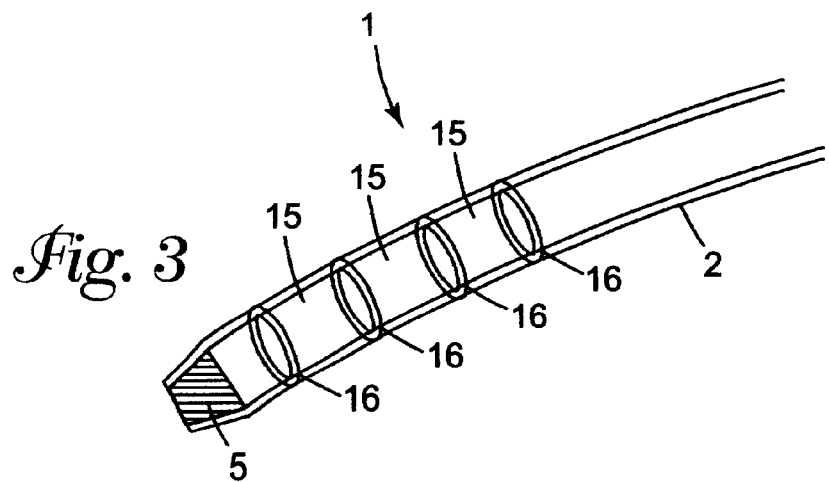
FIG. 3 is a view of another embodiment of the device according to the present invention. The view shows the disposition of microcoil elements at the distal tip of the drug delivery device.

With reference to FIG. 3 of the drawings, in the method of the invention, the delivery and distribution kinetics of intracerebrovascular, intrathecal, and intraparenchymal injections or infusions of drug agents, and/or other diagnostic or therapeutic media can be monitored quantitatively and non-invasively using realtime contrast-enhanced magnetic susceptibility and diffusion-weighted MR imaging.

Another preferred aspect of construction of the delivery device 1 comprises the technology of Truwit and Liu described above where said device comprises a sheath or housing 2 comprising an element having at least one pair of opposed RF receiver microcoils 16 having a space 15 between each microcoil 16 of said pair of microcoils. The coils of said microcoils 16 may have diameters of less than 2.4 mm. The device may also comprise an element having at least one pair of opposed RF receiver microcoils having a space between each microcoil of said pair of microcoils, said RF receiver microcoils each comprising at least three individual coils, said at least three individual coils of said microcoils having spacing between adjacent microcoils so that spacing between at least two pairs of individual coils within said microcoils differ by at least 10%. Circuitry may be insulated within the device by providing the wires and circuits within different layers in a coaxial layering of components within the catheter. The device may also comprise a device with an element having at least one pair of opposed RF receiver microcoils having a space between each microcoil of said pair of microcoils, the RF receiver microcoils each comprising at least three individual windings, the at least three individual windings of said microcoils having spacing between adjacent windings so that spacing between at least two pairs of individual windings within the microcoils differ by at least 10%. A magnetic tip 5 is shown for use with nonlinear magnetic stereotaxis.

The entire coil can be a composite. In another words, the entire imaging coil can be made of multiple coil elements connected in series or in a phased array fashion for simultaneous imaging at multiple locations along a catheter. All of these multiple coils can be similar or different in their geometrical shape. The imaging coil can also be non-local. That is, the coil can be spatially distributed along a significant length of a catheter (especially by consideration of modeling as shown above). For this purpose, there are many choices for the active coil components: twisted wire, two parallel wire, coaxial cable, combinations of these, etc.

In addition to the variety available in the selection of the imaging coil component, various other components, such as micro-electrodes can be incorporated in the device for cell or membrane potential measurement, pressure/flow monitoring or other physiological monitoring and/or electrophysiological and/or stimulating purposes.

For optimal signal to noise ratio (SIN) or minimal resulting noise figure, the MR signal detected would preferably have an immediate amplification (e.g., preamplification) in a location as close as possible to the coil element. The practical catheter geometry does not provide enough room for using any conventional amplification components. For the purpose of minimizing the size of the electronic components which will be used for various signal preconditioning processes such as pre-amplification, we have introduced an integrated circuit module in close proximity to the imaging module. The integrated circuit module includes a pre-amplification device (or unit at RF frequency) and other auxiliary devices silicon or other semiconductor fabricated on a chip, which is preferably less than 4 $mm^2$ in size. The same integrated circuit module is preferred to be packaged in a small non-magnetic casing compatible in shape with a given instrument design. One of the most simple units may contain only a single FET element. With the help of the integrated circuit technology, more elements can be incorporated into one single silicon or other semiconductor module for building more complex circuitry to achieve a better performance.

The preferred transmission module is a portion of the flexible cable along the catheter for transmitting the RF signal detected for MR imaging from the coil to a remote terminal for firter signal amplification and other required processing. In preferred design contemplations, all of the components of the cable are integrated into the catheter. One of the desired requirements for the cable is that it will introduce a minimal noise contamination as well as a low signal attenuation to the minute MR signal. The other desired requirement for the cable is that it will introduce a minimal hindrance to the flexibility and the stiffness of a catheter. For achieving these requirements, there are a number of the possible alternatives for the device as follows:

1) A tri-coaxial cable (a cable with a center line conductor surrounded by two concentric layers of shielding material). One variation of the cable is that the center conductor is wound in a helical fashion along the center axis of the cable.
2) A shielded twisted wire cable (a cable with two twisted wires at the center surrounded by a concentric layer of shielding material). One variation of the cable is that the two wires are wound in a spiral or helical fashion along the center axis of the cable.
3) A shielded parallel bi-polar cable (a cable with two parallel bi-polar wires placed symmetrically with respect to the center axis surrounded by a concentric layer of shielding material). One variation of the cable is that the two wires parallelly are wound in a spiral or helical fashion along the center axis of the cable.

The shielding layer can be a layer of braided thin conductive wires as well as a layer of metallic film, or any other shielding material (which may be grounded if desired) as understood in the art which may be provided in a dimension compatible with the practice of the present invention.

Yet another useful design is a concept of putting all the elements at the remote unit (or distal end). The schematic circuit diagram shown above in FIG. 3 includes an imaging coil (micro or macro), transmission line, phase shift network, tuning and decoupling circuit and balance (i.e., balanced/unbalanced impedance matching transformer). The Z denotes a tuning element (L or C) as a part of the decoupling circuit. The combined transmission line and phase shift network exhibits a quarter or half wavelength property.

The remote matching unit represents a device placed at the remote end of the device. This remote unit can be used as an extra tuning device for the imaging coil at the tip as well as a detuning (or decoupling) device. The remote match unit takes the effective impedance transformation of the transmission unit into consideration for the coil impedance matching and frequency tuning. In this design, both the transmission wire and the remote unit are used for accomplishing the tuning and detuning. In order to take advantage of the property of the transmission wire, the wire with a quarter wave or half wave length of the radio frequency of interest is used. Otherwise a transmission wire with a phase shift network which shows the same effective quarter wave or half wave length behavior can be used. The coil tuning can be accomplished with a capacitor or inductor. In addition, the size of the unit is not constrained geometrically. Since the device size for this module is not an issue, more conventional electronic components can be used. Depending on a specific design, the remote unit can be very important or of no importance.

Finally, the catheter tip has a stabilization mechanism incorporated. The preferred stabilization unit can be mechanically driven, or made of memory metal and controlled with an externally applied voltage signal.

As previously noted, it may be desirable to remove the magnetic tip used in the nonlinear magnetic stereotaxis positioning and guidance of the delivery device during the MR imaging and visualization step. It may also be desirable to be able to move that magnetic tip back into a movement effective position after the MR imaging to assist in further guidance or movement of the delivery device. This can be effected by any form of attachment or engagement of the tip to the catheter wherein the tip can be released or repositioned and then returned to an attached arrangement to the tip which attachment is of sufficient security as to enable movement, torque and application of directing or motivating forces to the catheter or delivery device. For example, in the simplest mode, the tip may be secured to the distal end of the device by tension on an elongated element holding the tip against an opening with a smaller diameter of the opening to the cross-section of the tip. The tip may be moved from the distal end by pulling on the elongated element, and then returned to the distal end after MR visualization by applying pushing tension on the elongated element again. Microminiature circuitry may also be used with the distal end to move the tip in a similar manner. A balloon system may be used whereby inflation of a balloon (with the tip on a surface of the balloon) will cause the expansion of the balloon to move the tip the expanded diameter of the balloon. A threaded engagement of the tip on the distal end of the delivery device (or at another guidance effective position) may be used, with unthreading, by the application of torque to the tip that may be used to temporarily free the tip, and reverse torque used to rethread the tip. This may be particularly effective where the tip lies completely within a threaded lumen, and rotation of the tip causes the tip to move in the desired direction within the lumen, first out of the image zone and then back into a desired position relative to effective guidance of the delivery device. This is most effective where movement out of the image zone would be in a direction away from the distal end of the tip. The tip may be slidably positioned on an outside surface or inside surface of the delivery device, and moved by appropriately applied forces back and forth over the surface of the delivery device. Where there is a porous or open area in the drug delivery device for allowing perfusion of drug along the sides of the device, the slidable tip may have a combined effect of non-linear magnetic stereotaxis guidance tip and protective cover/timed drug release activator for the delivery device.

As noted, microcircuitry may be used near or distant from the movable tip as a drive engine for any mechanical engagement to physically move the tip and reposition the tip, if desired. Material used to move the tip, secure the tip or the like, is preferably not strongly responsive to magnetic fields, and would preferably comprise polymeric or composite materials.

Figure 4A:
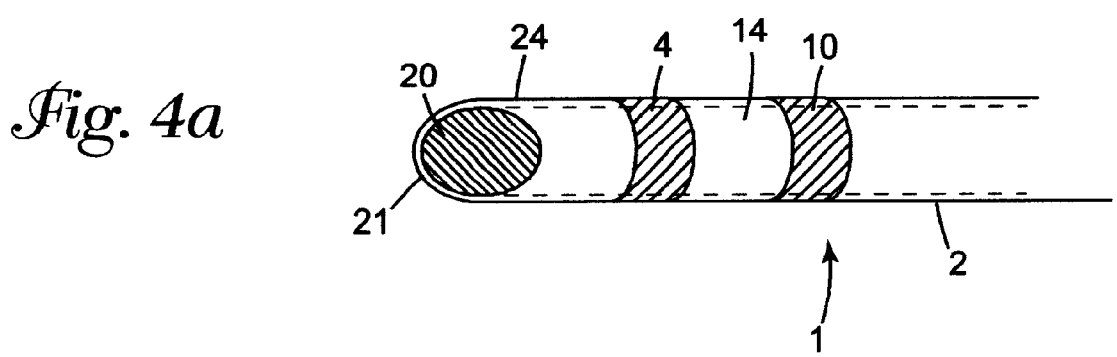
FIGS. 4a and 4b show the positioning of magnetic tips at the distal end of a delivery device in two of many embodiments of the present invention.
Figure 4B:
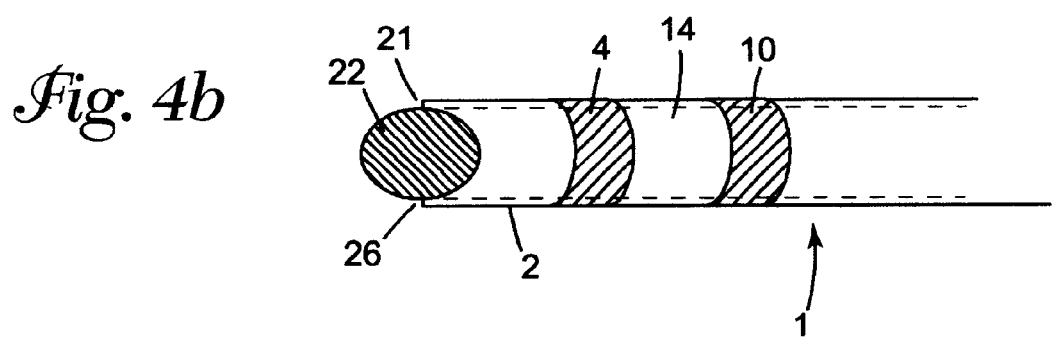

FIG. 4a shows a device 1 with a housing 2, a magnetic tip 20 nestling in the distal end 21 of the device 1 against an inside surface 24 of the housing 2. Marker areas 4 and 10 are shown separated over the lumen 14 of the device 1. FIG. 4b shows a different device 1 with an opening 26 at the distal end of the device 1.

We claim:

1. A method of delivering a material selected from the group consisting of drug agent and diagnostic agent by selective infusion or retroperfusion comprising the steps of:
    a) positioning a delivery device by a process selected from the group consisting of nonlinear magnetic stereotaxis and intra-operative magnetic resonance imaging-based guidance;
    b) verifying the location of said device via magnetic resonance (MR) imaging, and
    c) delivering said material by infusion or retroperfusion through said delivery device with real time visualization of said delivering via magnetic resonance imaging; wherein said verifying is done after positioning of said delivery device, and delivering said material is performed after verifying the location of said delivery device, wherein after said delivery of said material, magnetic resonance imaging visualizes the movement of said material through tissue, and wherein after visualizing the movement of said material through tissue, magnetic resonance imaging is temporarily halted, said delivery device is repositioned, and magnetic resonance imaging is restarted.

2. The method of claim 1 wherein the delivery device comprises an MR-visible catheter.

3. The method of claim 2 wherein said positioning of said delivery device occurs either within a brain's parenchyma or within cerebrovasculature.

4. The method of claim 1 in which an MR-visible and radio-opaque drug delivery device is used to treat cerebral lesions by targeted intraparenchymal injection or infusion of therapeutic agents.

5. The method of claim 4 wherein said therapeutic agents are selected from the group consisting of neuropeptides and monoclonal antibodies, gene therapies, and growth factors.

6. The method of claim 1 in which an MR-visible delivery device is employed for acute intracerebroventricular drug delivery or chronic acute intracerebroventricular drug delivery.

7. The method of claim 6 wherein said drug delivery comprises a procedure including a step selected from the group consisting of injection and infusion and wherein said injection or infusion is effected with at least one material selected from the group consisting of neuropeptides, monoclonal antibodies, growth factors, and therapeutic agents linked to blood-brain and CSF-brain transport vectors.

8. The method of claim 7 wherein said therpeutic agents comprise liposomes or endothelial permeabilizing agents.

9. The method of claim 1 in which an MR-visible delivery device is used to assist in monitoring by MR visualization changes in the composition of extracellular fluid or concentrations of administered drug agents at intracerebroventricular or intraparenchymal brain loci.

10. The method of claim 1, where an MR-compatible osmotic pump is connected via flexible MR-compatible tubing to a variable-length concentric MR-visible microdialysis probe with a molecular weight cut-off membrane or other infusion device which is directed by a procedure comprising nonlinear magnetic stereotaxis with subsequent MR verification of the location of the device at the site of a lesion within the central nervous system.

11. The method of claim 10 where the osmotic pump circulates a therapeutic drug solution containing an MR-visible contrast agent through walls of a dialysis fiber or other infusion device into the brain at rates between 0.01 nanoliters per hour to 10 microliters per minute.

12. The method of claim 1, where an MR-visible solution is provided by said delivery device, and said MR-visible solution comprises sterically stabilized liposomes, with lipophilic or hydrophilic chelators, or double-label liposomes that chelate a T2-sensitive metal ion within an internal aqueous space and another T1-sensitive metal ion on an outside membrane surface, or liposomes which contain 100–1000 nm bubbles of gas as a contrast agent.

13. The method of claim 1 wherein said delivering of a material selected from the group consisting of biologically active agent, diagnostic agent, and therapeutic agent is performed under real time observation by magnetic resonance imaging which generates a visible image of concentration levels of said material within the tissues of a patient.

14. The method of claim 13 wherein said visible image of concentration levels is generated by data from magnetic resonance imaging relating to apparent diffusion coefficients.

15. The method of claim 1 wherein said delivering of a material is performed under real time observation by observing with magnetic resonance imaging a visible image within an area or volume comprising the tissue or tissues of said living patient, the area or volume including a material delivery device delivering at least some material by the material delivery device into the area or volume comprising tissue of a living patient, and observing a change in property of said visible image of the area or volume comprising tissue of a living patient while said material delivery device is still present within the area or volume.

16. The method of claim 1 wherein said infusion or retroperfusion of material is viewed in real time or near real time.

17. The method of claim 1 wherein verifying is performed in real time or near real time.

18. The method of claim 1 wherein said delivery device is repositioned by nonlinear magnetic stereotaxis.

19. A method of delivering a drug selected by selective infusion or retroperfusion comprising the steps of:
    a) positioning a delivery device by a process selected from the group consisting of nonlinear magnetic stereotaxis and intra-operative magnetic resonance imaging-based guidance;
    b) verifying the location of said device via magnetic resonance (MR) imaging, and
    c) delivering said drug by infusion or retroperfusion through said delivery device; in which method an MR-visible drug delivery device is used to treat tumors of a brain by acute, subacute or chronic infusion, said drug being selected from the group consisting of therapeutic drug agents, neurotoxins, anti-angiogenesis factors, embolotherapy agents, anti-emetics, anti-nausea agents, genetic therapies, anti-tunoral agents and antineoplastic agents, said verifying and delivering being performed under real time MR-visualization;

wherein said verifying is done after positioning of said delivery device, and delivering said material is performed after verifying the location of said delivery device, wherein after said delivery of said material, magnetic resonance imaging visualizes the movement of said material through tissue, and wherein after visualizing the movement of said material through tissue, magnetic resonance imaging is temporarily halted, said delivery device is repositioned, and magnetic resonance imaging is restarted.

20. A method of delivering a material selected from the group consisting of dignostic agent and therapeutic agent by selective infusion or retroperfusion comprising the steps of:

a) positioning a delivery device by nonlinear magnetic sterotaxis;

b) verifying the location of said delivery device via magnetic resonance imaging, and c) subsequently delivering said material by infusion or retroperfusion through said delivery device with real time visualization of said delivering, wherein after delivery of said material, magnetic resonance imaging visualizes the real time movement of said material through tissue, wherein after visualizing the movement of said material through tissue, magnetic resonance imaging is temporarily halted, said delivery device is repositioned by non-linear magnetic stereotaxis, and magnetic resonance imaging is restarted.

21. A method of delivering a material selected from the group consisting of diagnostic agent and therapeutic agent by selective infusion or retroperfusion comprising the steps of:

a) positioning a delivery device by a process selected from the group consisting of nonlinear magnetic stereotaxis and intra-operative magnetic resonance imaging-based guidance;

b) verifying the location of said device via magnetic resonance (MR) imaging, and c) delivering said material by infusion or retroperfusion through said delivery device;

wherein said verifying is done after positioning of said delivery device, and delivering said material is performed after verifying the location of said delivery device, wherein after said delivery of said material, magnetic resonance imaging visualizes the movement of said material through tissue, and wherein after visualizing the movement of said material through tissue, magnetic resonance imaging is temporarily halted, said delivery device is repositioned, and magnetic resonance imaging is restarted.

* * * * *